(12) United States Patent
Rauch et al.

(10) Patent No.: US 11,992,500 B2
(45) Date of Patent: May 28, 2024

(54) USE OF METHYLATION INHIBITORS FOR THE TREATMENT OF AUTOIMMUNE DISEASES

(71) Applicant: Rush University Medical Center, Chicago, IL (US)

(72) Inventors: Tibor A. Rauch, Oak Park, IL (US); Daniel M. Toth, Chicago, IL (US); Tibor T. Glant, Chicago, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 0 days.

(21) Appl. No.: 17/050,526

(22) PCT Filed: Apr. 26, 2019

(86) PCT No.: PCT/US2019/029381
§ 371 (c)(1),
(2) Date: Oct. 26, 2020

(87) PCT Pub. No.: WO2019/210192
PCT Pub. Date: Oct. 31, 2019

(65) Prior Publication Data
US 2021/0128600 A1    May 6, 2021

Related U.S. Application Data

(60) Provisional application No. 62/762,263, filed on Apr. 26, 2018.

(51) Int. Cl.
| | | |
|---|---|---|
| *A61K 31/7068* | (2006.01) | |
| *A61K 31/353* | (2006.01) | |
| *A61K 31/4035* | (2006.01) | |
| *A61K 31/4045* | (2006.01) | |
| *A61K 31/496* | (2006.01) | |
| *A61K 31/548* | (2006.01) | |
| *A61P 19/02* | (2006.01) | |
| *A61K 45/06* | (2006.01) | |

(52) U.S. Cl.
CPC ........ *A61K 31/7068* (2013.01); *A61K 31/353* (2013.01); *A61K 31/4035* (2013.01); *A61K 31/4045* (2013.01); *A61K 31/496* (2013.01); *A61K 31/548* (2013.01); *A61P 19/02* (2018.01); *A61K 45/06* (2013.01)

(58) Field of Classification Search
CPC .... A61K 45/06; A61K 31/52; A61K 2300/00; A61P 19/02
See application file for complete search history.

(56) References Cited

U.S. PATENT DOCUMENTS

2016/0206609 A1    7/2016   Schubert et al.

FOREIGN PATENT DOCUMENTS

CN    107158019 A    9/2017

OTHER PUBLICATIONS

FDA (Guidance for industry; pp. 1-27, Jul. 2005).*
International Preliminary Report on Patentability, issued in PCT/US2019/029381, dated Nov. 5, 2020.
International Search Report, issued in PCT/US2019/029381, dated Jun. 26, 2019.

* cited by examiner

*Primary Examiner* — Pancham Bakshi
(74) *Attorney, Agent, or Firm* — Barnes & Thornburg LLP

(57) ABSTRACT

Described herein is a method for treating an autoimmune disease in a patient including administering to the patient in need thereof, a pharmaceutically effective amount of an epigenetic enzyme inhibitor.

11 Claims, 14 Drawing Sheets

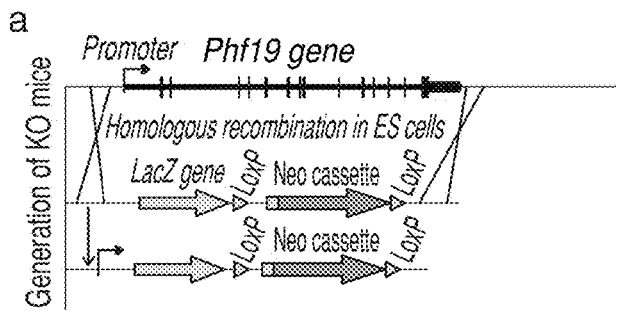
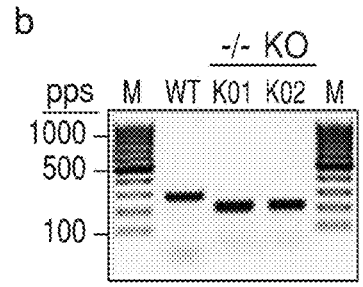
FIG. 8(A)  FIG. 8(B)
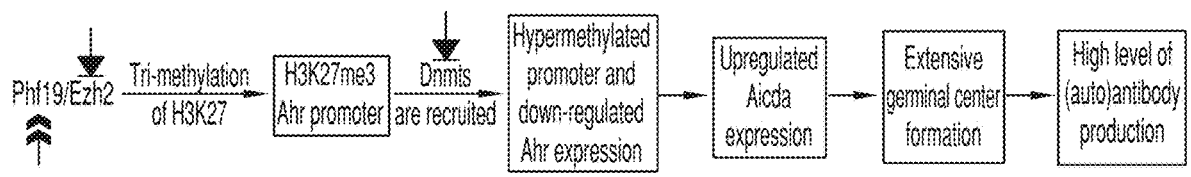
FIG. 9
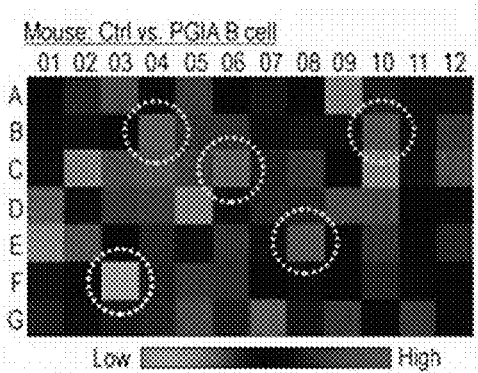
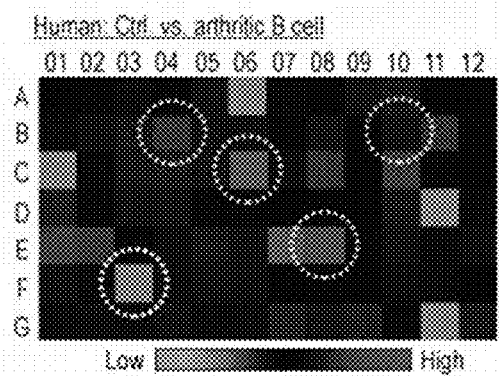
FIG. 10(A)  FIG. 10(B)

USE OF METHYLATION INHIBITORS FOR THE TREATMENT OF AUTOIMMUNE DISEASES

RELATED APPLICATIONS

This application is a National Stage application of International Application No. PCT/US2019/029381, filed Apr. 26, 2019, which claims the benefit of U.S. Provisional Application No. 62/762,263, filed Apr. 26, 2018, both of which are incorporated by reference herein in their entirety.

FEDERALLY SPONSORED RESEARCH OR DEVELOPMENT

This invention was made with government support under federal grant number R21-AR064948-01 awarded by National Institutes of Health. The government has certain rights in the invention.

BACKGROUND

Autoimmune diseases are caused by an overactive immune system where the body attacks and damages its own tissues. Rheumatoid arthritis (RA) is a chronic inflammatory autoimmune disease where the body's immune system produces antibodies that attacks synovial joints, leading to inflammatory destruction of articular cartilage and bone leading mainly to pain, stiffness, swelling and limited motion and function of affected joints. Although RA primarily affects the joints, extra-articular complications occur in 15-25% of RA patients, most frequently affecting functions of the skin, lungs, kidneys and the heart.

Rheumatoid arthritis affects approximately 1% of the adult human population, and represents a major cause of disability. RA is considered a polygenic disease with strong immunogenetic components because various immune cells (T and B lymphocytes, macrophages, dendritic cells) are involved. Rheumatoid arthritis is a T cell regulated and B cell mediated progressive autoimmune disease that primarily attacks synovial joints. B cells contribute to RA pathogenesis by producing a characteristic set of inflammatory cytokines and expressing high level of self-reactive antibodies. This ultimately leads to destruction of the joints.

Genetic disposition makes a substantial but incomplete contribution to the risk of developing arthritis. Identification of disease-promoting genes and understanding of the molecular mechanisms involved are prerequisites for successful therapeutic interventions. Genome-wide association studies (GWAS) have identified risk loci carrying a number of genes implicated in RA pathogenesis. Genetic disposition is undeniably a decisive component for RA susceptibility; however, studies with monozygotic twins have drawn attention to the importance of epigenetic factors that mediate interactions between genes and the environment.

Recent studies prove that environmental factors can contribute to the etiology of arthritis. Environmental factors such as cigarette smoke, certain diet components and toxins can significantly affect gene regulation via epigenetic factors and are frequently implicated as non-genetic risk factors in the pathogenesis of RA. Epigenetic factors form links between the environment and genes by sensing and transmitting external signals into the nucleus to generate the most appropriate gene expression profile of the cell. Environmental factors can significantly contribute to the etiology of RA via epigenetic mechanisms. Methylation of cytosines is a ubiquitous feature of eukaryotic genomes that is fundamental to cellular differentiation processes and control of transcriptional potential. DNA methylation patterns can be inherited and influenced by the environment, diet, aging process, and diseases. Environmental toxins induce epimutations in the immune cell methylomes, which includes alteration of DNA and histone methylation profiles.

Currently, there is no cure for RA, but treatments can provide alleviation of symptoms and modify disease progression. Despite intense investigations, effective therapy against RA is still unavailable. The goals of treatment are complex, including mitigation of pain, reducing or halting joint destruction and preventing extra-articular complications. Therefore, in most cases optimal disease treatment can only be achieved through combined application of different drugs. When a combination of traditional disease-modifying anti-rheumatic drugs (DMARDs), non-steroid anti-inflammatory drugs (NSAIDs), and low-dose glucocorticoids does not provide satisfactory response, highly specific biologics are introduced into the treatment regimen. Classical DMARDs and NSAIDs are usually small molecules that broadly affect many components of the immune system, whereas rationally designed biologics (e.g., anti-TNFα, anti-IL-1β, IL-6 antagonist) specifically inactivate or neutralize key mediators of the inflammatory processes. Therefore, understanding the mechanism of the disease process of RA and development of effective reactivation of silenced activator as a therapeutic approach to alleviate symptoms are of paramount importance.

SUMMARY

A method for treating an autoimmune disease in a patient is provided. The method includes administering to the patient in need thereof, a pharmaceutically effective amount of an epigenetic enzyme inhibitor. In some aspects, the autoimmune disease is selected from polyarthritis, rheumatoid arthritis, systemic lupus erythematosus, inflammatory bowel disease, ulcerative colitis, multiple sclerosis, type 1 diabetes mellitus, Sjogren's syndrome, graft-versus host reactions, psoriasis, myasthenia gravis, vasculitis, Crohn's disease, Guillain-Barre syndrome, Graves' disease, pernicious anemia, chronically active hepatitis and Hashimoto's thyroiditis.

In yet other aspects, method for treating an autoimmune disease in a patient includes administrating to the patient in need thereof, a pharmaceutically effective amount of an epigenetic enzyme inhibitor, wherein the epigenetic enzyme inhibitor is a DNA methylation inhibitor. In a further aspect, the epigenetic enzyme inhibitor is a histone methylation inhibitor.

BRIEF DESCRIPTION OF THE DRAWINGS

FIGS. 1(A)-(F) show arthritis-associated DNA methylation and gene expression changes in mouse B cells. FIG. 1(A) illustrates a heatmap of DNA methylation profile analysis of annotated mouse promoters and CpG islands (CGIs) generated using MIRA-chip. Hypomethylated gene cluster is labeled with green bar on the side. Yellow bar refers to slight differential methylation showing genes. Red side-bar represents de novo hypermethylated promoter cluster. FIG. 1(B) shows a heatmap of arthritis-associated gene expression changes in mouse B cells. FIG. 1(C) shows PGIA-linked de novo hypermethylation in Ahr gene promoter region. MIRA-detected DNA methylation levels are represented by vertical bars. Location of the first exon of Ahr gene and direction of transcription is labeled on the top (black box and arrow). FIG. 1(D) is a chart showing relative DNA methylation levels of Ahr promoter and arthritic B cell genomic DNA samples as analysed by MIRA. FIG. 1(E) is a chart showing results of quantitative analysis (RT-qPCR) of Ahr gene expression in control, in B cells of PGIA mice, and in A20 B cell line. (n=3 mice per group or n=3 independent cell cultures). Measured Ct values were normalized to Actin-βvalues. Values are the mean±SEM. * P<0.05,  P<0.01. FIG. 1(F) illustrates an assessment of global DNA methylation. DNA methylation levels of genomic DNA samples from mice with proteoglycan-induced arthritis (PGIA) were compared to samples control (adjuvant-injected) mice. FIG. 1(G) is a chart showing Arthritis-associated AhR gene expression. AhR expression was investigated in DMARD naive RA patients (n=47) and control subjects (n=19) using qRT-PCR. Measured Ct values were normalized to Actin β values. Values are the mean±SEM.  P<0.01. FIG. 1(H) is a chart showing DNA methylation analysis of upstream regulatory element C of AhR gene. Genomic DNA isolated from 10 control and 10 DMARD-naive RA patients were investigated using MIRA method. Measured Ct values were normalized to GAPDH values. Values are the mean±SEM. * P<0.05. FIG. 1(L) is a chart showing Reactivation of AhR gene expression. A20 cells were treated with 5, 10 and 15 μM AzaC for 48 and 78 hours before RNA isolation. Quantitative RT-PCR analyses were conducted on reverse transcribed samples. Bars represent mean±SEM values of three independent experiments. Ct values were normalized to Actin-0 values. * P<0.05, ** P<0.001. FIG. 1(M) is a Western blot image of AhR in AzaC treated A20 cells. A20 cells were treated with 10 μM AzaC for 72 hours before harvesting and subcellular fractionation. Gapdh and Lamin b1 were used as loading controls for cytoplasmic and nuclear fractions. Western blots represent 1 of 3 independent experiments. C, AhR translocated in nuclei triggers elevated expression of Cyp1a1 gene. Experimental design was identical as described in section A. FIG. 1(N) is a Quality control analysis chart of DNA methylation-related microarray data sets.

FIGS. 2(A)-(B) are chart of data deomonstrating that AzaC-treatment increased Arnt and RelB (potential Ahr interacting factors), expression in A20 cells. FIG. 2(C) is a Venn diagram of PGIA-specific B cell genes, MZ and GC B-cell specific genes. Asterisk-labeled set of 6 genes (PGIA down & MZ B cells) contains Ahr. #-labeled set of 20 genes harbors Aicda. FIG. 2(D) is a chart showing that AzaC-treatment triggers downregulated expression of Aicda in A20 cells. FIG. 2(E) demonstrates that AzaC treatment reduces Aicda level in cytoplasmic fraction of A20 B cells. Gapdh used as cytoplasmic and Lamin β (Lmnb) for nucleus-specific loading controls. FIG. 2F illustrates alignment of ChIP-sequence defined Ahr consensus (top) versus the algorithm-predicted (bottom) Ahr-binding element. FIG. 2(G) is an image of electrophoretic mobility shift assay (EMSA) showing putative intronic Ahr-binding site in vitro binds Ahr Ahr-binding consensus competes out Ahr binding at 50-fold molar excess. FIG. 2(H) is a chart showing results of Chromatin immunoprecipitation (ChIP) analysis of Ahr binding in vivo to the intronic silencer region of Aicda. FIG. 2(K) describes Aicda expression at 24 hours and 48 hours after Aza-C treatment. FIG. 2(L) describes both Ahr and Aicda expression using AzaC-treatment with and without shRNA.

FIG. 3(A) is a chart depicting severity of arthritis score in relation to prophylactic treatment of mice with AzaC. AzaC-treatment (i.p.) started 10 days before the expected PGIA onset, and administered every other day till the end of the study. Control group received saline solution. FIG. 3(B) depicts therapeutic AzaC treatment. Mice received AzaC treatment every other day after the first symptoms of arthritis till the end of the study. Control group received saline. FIG. 3(C) is a chart illustrating that AzaC-treatment reduced DNA methylation level of Ahr promoter detected by MIRA, which was accompanied by increased Ahr expression (FIG. 3(D)), and FIG. 3(E) depicts downregulation of Aicda expression as monitored by RT-qPCR. FIG. 3(F) illustrates that downregulated Aicda expression induced impaired CSR. Germline transcripts (Iji-Cji and Iy1-Cy1) and post-recombination transcripts (Iji-Cy1) of IgG locus were quantified by RT-qPCR in splenic B cells of mice with PGIA (untreated) and AzaC-treated arthritic mice. FIG. 3(G) is a chart showing human PG-specific IgG1 concentration as determined by ELISA in sera of untreated mice with PGIA and AzaC-treated PGIA mice. FIGS. 3(H)-(I) depict macroscopic images of hind limbs and histopathology of corresponding ankle joints of control (non-immunized) mice as shown in FIG. 3(H); FIG. 3(I) shows macroscopic images of hind limbs and histopathology of corresponding ankle joints of arthritic (un-treated) mice and FIG. 3(J) shows macroscopic images of hind limbs and histopathology of corresponding ankle joints of arthritic AzaC-treated mice. Arrows indicate bone marrow-eroding inflammatory tissues. Sections of decalcified hind paws of mice were stained with hematoxylin and eosin.

FIG. 4(A) is a chart showing Flow cytometric analysis of immature B cells (B220/CD45R+, IgD−/IgM+, CD23−) and plasma cells (B220/CD45low, CD138+) from bone marrow of PGIA mice and PGIA mice treated with AzaC. FIG. 4(B) shows flow cytometric analysis of MZ (B220/CD45R+, IgM+/IgDlow, CD23−) and follicular (B220/CD45R+, IgMlow/

IgD+, CD23+) B cells from spleen of PGIA mice and PGIA mice treated with AzaC. N=6 mice of each group. GC formation in lymph nodes (FIG. 4(C)) and in spleen (FIG. 4(D)). Red-B220, Green-GL7, Blue-CD4.

FIG. 5(A) is a chart showing differential expression of cytokines in arthritic B cells. Expression of pro- and anti cytokine genes were qRT-PCR analyzed in affinity purified splenic B cells from mice with PGIA and control animals. FIG. 5(B) shows Arthritis-linked expression of immunoglobulin genes in B cells. Figure(C) shows AzaC treatment altered cytokine gene expressions in A20 cells witj AzaC treatment. A20 cells were treated with 10 µM AzaC for 72 hours and qRT-PCR analyses were conducted on reverse transcribed samples. Bars represent mean±SEM values of three independent experiments. Ct values were normalized to Actin-0 values. * P<0.05, ** P<0.001.

FIG. 7(A) illustrates Phf19 and Ezh2 gene expression in mouse B cells from the spleens of adjuvant-injected controls (CTRL, white columns) and arthritic mice (PGIA, gray columns) (n=4). FIG. 7(B) depicts PHF19 and EZH2 gene expression in human PBMCs. The white bars represent healthy controls (CTRL, with baseline [1-fold] expression), and the gray bars show relative expression changes measured using qRT-PCR in the PBMCs obtained from healthy individuals (n=5) and treatment-naive RA patients (n=16) (*p<0.05, **p<0.01).

FIG. 8(A) is a diagram showing the generation of Phf19 Knock-out (KO) mice. In ES cells, the Phf19 gene was replaced with a targeting vector carrying the LacZ-Neo cassette. FIG. 8(B) shows PCR genotyping of Phf19 KO mice. WT mice carry the original Phf19 gene. KO1 and KO2 mice have no Phf19 alleles.

FIG. 9 illustrates the hypothesis for contribution of Phf19/Ezh2 genes to arthritis in mouse B cells. Red arrow points to a GWAS-identified RA risk gene. Green arrows indicate druggable genes. (Dnmts—DNA methyltransferases).

FIGS. 10A-B illustrate arthritis-associated changes in the expression of epigenetic factors in arthritic mouse and human B cells. FIG. 10(A) shows PCR-array heatmaps of gene expression changes in mouse B cells and FIG. 10(B) shows PCR array heatmaps of gene expression changes in human B cells. Red squares indicate upregulated genes; green squares indicate downregulated genes. RNA samples from arthritic B cells (PGIA or RA) were compared to that from control (adjuvant-treated or healthy human subject). Similarly upregulated genes are B04 (Cbx5), B11 (Dnmt1), C06 (Ezh2) and E08 (Phf19); the downregulated gene is F03 (Ring1). The differentially expressed genes shared between PGIA and RA are circled.

DETAILED DESCRIPTION

Figure 1A:
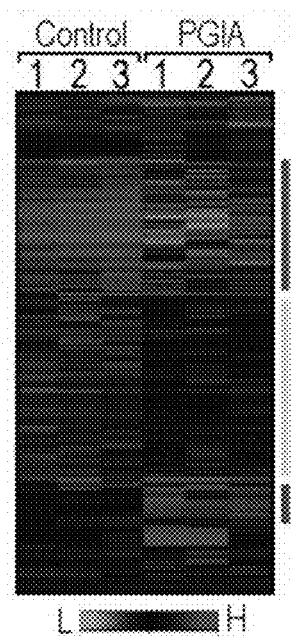
FIGS. 1A-1N.
Figure 1B:
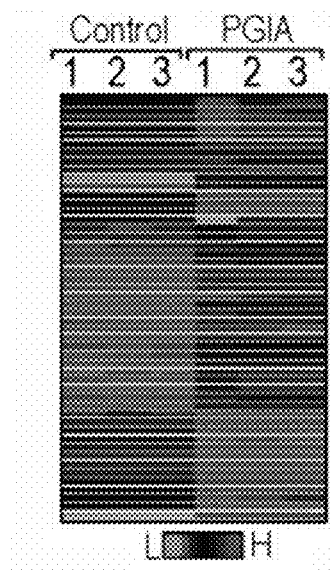

Various embodiments, aspects, figures and illustrations described herein are directed to advantageous pharmaceutical combinations and methods of treatment for autoimmune diseases, such as rheumatoid arthritis which employ treatment with methylation inhibitors. The compositions and methods provided are exemplary and are not intended to limit the scope of any of the specified embodiments. All of the various embodiments, aspects, and options disclosed herein can be combined in any and all variations or iterations.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

An "autoimmune disease" as used herein is a disease or disorder arising from and directed against an individual's own tissues. Examples of autoimmune diseases or disorders include, but are not limited to arthritis or polyarthritis or rheumatoid arthritis (RA), psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis *nodosa*), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), and coronary artery disease. In some aspects, the autoimmune disease may be selected from polyarthritis, rheumatoid arthritis, systemic lupus erythematosus, inflammatory bowel disease, ulcerative colitis, multiple sclerosis, type 1 diabetes mellitus, Sjogren's syndrome, graft-versus host reactions, psoriasis, myasthenia gravis, vasculitis, Crohn's disease, Guillain-Barre syndrome, Graves' disease, pernicious anemia, chronically active hepatitis and Hashimoto's thyroiditis, and in particular rheumatoid arthritis.

The terms "PGIA," "PGIA model" and "PG-induced arthritis" are used interchangeably herein and refer to cartilage proteoglycan (aggrecan)-induced polyarthritis in BALB/c mice that is characterized by chronic inflammation and destruction of joint tissues similar to that observed in human rheumatoid arthritis. PGIA in BALB/c mice shows many similarities to human rheumatoid arthritis (RA), as indicated by clinical assessments, immunological tests and histopathology of joints. The development of arthritis in BALB/c mice, initiated by i.p. injection with glycosaminoglycan-depleted human fetal cartilage proteoglycan (HFPG), is associated with the expression of both cell-mediated immunity and autoantibody production to the mouse 'self' cartilage PG. The onset of PGIA is very predictable; the first signs of arthritis (redness and swelling of the paws—acute phase) can be observed 9-10 days after the third immunization. Seven days after the onset of arthritis, the redness and swelling of the paws gradually declines; meanwhile, articular joints are destroyed and ankylosed (chronic phase). PGIA is an excellent mouse model of seropositive progressive polyarthritis such as RA.

The term "Histone methyltransferase" (HMT) as used herein refers to histone-modifying enzymes, for example, histone-lysine N-methyltransferases and histone-arginine N-methyltransferases, that catalyze the transfer of one, two, or three methyl groups to lysine and arginine residues of histone proteins. This process can result in either the activation or repression of transcription. The attachment of methyl groups occurs predominantly at specific lysine or arginine residues on histones H3 and H4.

The term "DNA Methyltransferases" (DNMTs), and "DNA methylase" are used interchangeably herein and refer to enzymes capable of transferring a methyl group from the universal methyl donor, S-adenosyl-L-methionine (SAM), to the 5-position of cytosine residues in DNA. The term DNA Methyltransferase includes but is not limited to members of the DNMT family, including DNMT1, DNMT3A, DNMT3B and DNMT3L. DNA methyltransferase (DNA MTase) family of enzymes catalyze the transfer of a methyl group to DNA. DNA methylation is a postreplicative covalent modification of DNA that is catalyzed by the DNA methyltransferase enzyme (MeTase) (Koomar et al., 1994, Nucl. Acids Res. 22:1-10; and Bestor et al., 1988, J. Mol. Biol. 203:971-983). In vertebrates, the cytosine moiety at a fraction of the CpG sequences is methylated (60-80%) in a nonrandom manner generating a pattern of methylation that is gene and tissue specific. Methylation in regulatory regions of a gene is correlated with a repressed state of the gene. Recent data suggest that DNA methylation can repress gene expression directly, by inhibiting binding of transcription factors to regulatory sequences or indirectly, by signaling the binding of methylated-DNA binding factors that direct repression of gene activity.

The terms "inhibitor" and "blocker" are used interchangeably herein and refer to an agent that reduces expression of a polypeptide or polynucleotide target or binds to, partially or totally blocks stimulation, decreases, prevents, delays activation, inactivates, desensitizes, or down regulates the activity of a polypeptide or polynucleotide target. An inhibitor can neutralize activity (e.g., prevent binding and activation by a natural ligand) or actively reduce activity. Inhibitors can be of synthetic or biological origins. They can be organic, inorganic molecules, peptides, antibodies, or antisense RNA.

The terms "epigenetic enzyme inhibitor,""methylation blocker" and "methylation inhibitor" are used interchangeably herein and refer to DNA methyltransferase inhibitor, DNA methylation inhibitor, histone methyltransferase inhibitor, histone modification inhibitor, and histone methylation inhibitor. Inhibitors may have anti-proliferative activity. Inhibitors can reactivate the expression of genes that have been repressed by DNA methylation. These are of two types, nucleoside analog inhibitors (AzaC and dAzaC) and non-nucleoside analog inhibitors. Non-nucleoside analog inhibitors comprise caffeic acid, chlorogenic acid, epigallocatechin gallate, hydralazine hydrochloride, procainamide hydrochloride, procaine hydrochloride, and RG108. "Methylation inhibitors" are chemical entities or molecules that can inhibit expression of the targets and/or biological activity of the targets. Targets of methylation inhibitors as used herein may include DNA methyltransferase, histone methyltransferase, a protein, a peptide, or a ligand capable of methylating DNA or histone. Exemplary DNA methylation inhibitors comprise 4-Amino-1-(β-D-ribofuranosyl)-1,3,5-triazin-2(1H)-one (Azacitidine or AzaC), 2'-Deoxy-5-azacytidine, 4-Amino-1-(2-deoxy-β-D-ribofuranosyl)-1,3,5-triazin-2(1H)-one (5-aza-2'-deoxycytidine or dAzaC), N-[4-[(2-amino-6-methyl-4-pyrimidinyl)amino]phenyl]-4-(4-quinolinylamino)-benzamide (SGI-1027), epigallocatechin-3-gallate (EGCG), N-phthaloyl-1-tryptophan (RG108), caffeic acid, chlorogenic acid, hydralazine hydrochloride, procainamide hydrochloride, procaine hydrochloride, 2-Amino-6-[(4-bromo-2-thienyl)methoxy]-9H-purine) (lomeguatrib), and, ((R)—N-((4-Methoxy-6-methyl-2-oxo-1,2-dihydropyridin-3-yl)methyl)-2-methyl-1-(1-(2,2,2-trifluoroethyl)piperidin-4-yl)ethyl)-1H-indole-3-carboxamide (CPI-1205).

Exemplary histone methylation inhibitors comprise 1-cyclopentyl-N-[(1,2-dihydro-4,6-dimethyl-2-oxo-3-pyridinyl) methyl]-6-[4-(4-morpholinylmethyl)phenyl]-1H-indazole-4-carboxamide (EPZ005687), 7-[5-Deoxy-5-[[3-[[[[4-(1,1-dimethylethyl)phenyl] amino] carbonyl] amino]propyl] (1-methylethyl)amino]-β-D-ribofuranosyl]-7H-pyrrolo[2,3-d]pyrimidin-4-amine (EPZ004777), N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide (GSK126), N4-(1-benzylpiperidin-4-yl)-N2-(3-(dimethylamino)propyl)-6,7-dimethoxyquinazoline-2,4-diamine (E11), 2-(Hexahydro-4-methyl-1H-1,4-diazepin-1-yl)-6,7-dimethoxy-N-[1-(phenylmethyl)-4-piperidinyl]-4-quinazolinamine trihydrochloride (BIX01294), N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide (GSK343), N-[(1,2-dihydro-4,6-dimethyl-2-oxo-3-pyridinyl)methyl]-3-methyl-1-(1-methylethyl)-6-[6-(4-methyl-1-piperazinyl)-3- pyridinyl]-1H-indole-4-carboxamide (GSK503), N-[(1,2-dihydro-4,6-dimethyl-2-oxo-3-pyridinyl)methyl]-5-[ethyl (tetrahydro-2H-pyran-4-yl)amino]-4-methyl-4'-(4-morpholinylmethyl)-[1,1'-biphenyl]-3-carboxamide (EPZ6438), chaetocin, and ((R)—N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205).

As used in the description of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items, as well as the lack of combinations when interpreted in the alternative ("or"). The term "about," as used herein when referring to a measurable value such as an amount of protein, dose, time, temperature, enzymatic activity or other biological activity and the like, is meant to encompass variations of 20%, 10%, 5%, 1%, 0.5%, or even 0.1% of the specified amount.

METHODS OF TREATMENT

The terms "treating", "treat", or "treatment" as employed herein, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to a an autoimmune disease or a halting in the progression of an autoimmune disease such as rheumatoid arthritis.

The terms "dosage unit form," or "unit dose" as used herein, refers to physically discrete units suitable as unitary dosages, each unit containing a predetermined quantity of active ingredient calculated to produce the desired therapeutic effect either in association with or without a pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The term "dose" is generally contemplated to mean a therapeutically effective amount of the active ingredient or methylation inhibitor administered in a regimen. In some embodiments, the dose may be administered daily, several times a day, every other day, weekly, monthly or at other intervals deemed appropriate by the physician. The methylation inhibitor in a dose may comprise of either DNA methylation inhibitor, a histone methylation inhibitor or a combination thereof. Actual dosage levels of methylation inhibitor(s) may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

The terms "subject" and "patient" are used interchangeably herein, and refer to an animal, for example a human, to whom treatment for an autoimmune disease, such as RA, including therapeutic treatment or prophylactic treatment, with a pharmaceutical composition comprising a methylation inhibitor as disclosed herein is beneficial. The term "subject" or "patient" as used herein includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

"Pharmaceutically-acceptable" as used herein shall mean that the pharmaceutically active compound and other ingredients used in the pharmaceutical compositions and methods defined herein are suitable for use in contact with the tissues of humans and lower animals without undue toxicity, irritation, allergic response, and the like, commensurate with a reasonable benefit/risk ratio.

The expression "therapeutically effective amount" or "effective amount" refers to an amount of the antagonist which is effective for preventing or prophylaxis, ameliorating or treating the autoimmune disease in question. A "therapeutically effective amount" or "effective amount" of a substance is an amount sufficient to effect beneficial or desired results, including clinical results, and, as such, an "effective amount" or "therapeutically effective amount" depends upon the context in which it is being applied. In the context of administering a composition to treat or prevent rheumatoid arthritis, an effective amount of a methylation inhibitor is an amount sufficient to treat and/or ameliorate RA symptoms as well as decrease the severity or prevent a particular RA-related complications. The decrease can be a 10%, 20%, 30%, 40%, 50%, 60%, 70%, 80%, 90%, 95%, 98% or 99% decrease in severity of complications. An effective amount can be administered in one or more administrations. A therapeutically effective amount of the methylation inhibitor(s) is contemplated to be; <70 mg/m$^2$/day; <60 mg/m$^2$/day; <50 mg/m$^2$/day; 40 mg/m$^2$/day; <30 mg/m$^2$/day; <20 mg/m$^2$/day; or 1-20 mg/m$^2$/day. A "therapeutically effective amount" or an "effective amount" for a particular subject may vary depending on factors such as the condition being treated, the overall health of the subject, the method, route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

The embodiments described herein provide several methods for treating or preventing an autoimmune disease in a patient. In an aspect of the embodiment, a patient is given a methylation inhibitor, the methylation inhibitor is either a DNA methylation inhibitor or a histone methylation inhibitor or a combination thereof. The DNA methylation inhibitor is selected from a group comprising AzaC, dAzaC, SGI-1027, EGCG, RG108, caffeic acid, chlorogenic acid, hydralazine hydrochloride, procainamide hydrochloride, procaine hydrochloride, lomeguatrib, and CPI-1205. The histone methylation inhibitor is selected from a group comprising EPZ005687, EPZ004777, GSK126, Ell, BIX01294, GSK343, GSK503, EPZ6438, chaetocin, and CPI-1205.

The inhibitor compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. They are of course given in forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "method of treating a disease or disorder" by administering a therapeutically effective amount of an inhibitor (e.g., a dose of a methylation inhibitor which inhibits methlation of DNA or histones) is directed to a method of treating a subject for an autoimmune disease comprising administering to the subject a methylation inhibitor or a histone methylation inhibitor. The DNA methylation inhibitor and histone methylation inhibitor and be administered singly or in combination. The DNA methylation inhibitor and a histone methylation inhibitor can be administered to the subject sequentially or simultaneously. A sequential administration includes (a) first administering a DNA methylation inhibitor followed by (b) administering a histone methylation inhibitor. An alternative sequential administration includes includes (a) first administering a histone methylation inhibitor followed by (b) administering a DNA methylation inhibitor. A simultaneous administration includes administering a DNA methylation inhibitor and a histone methylation inhibitor at the same time; or at substantially the same time.

When administration involves the separate administration of DNA methylation inihibitor and histone methylation inhibitor (e.g., sequential administration) of a first inhibitor (e.g., a DNA methylation inhibitor and a second compound (e.g., a histone methylation inhibitor), as described herein, the compounds are administered sufficiently close in time to have the desired therapeutic effect. For example, the period of time between each administration, which can result in the desired therapeutic effect, can range from minutes to hours and can be determined based on the properties of each compound such as potency, solubility, bioavailability, plasma half-life and kinetic profile. For example, the compounds can be administered in any order within about 24 hours of each other or within any time less than 24 hours of each other.

When a DNA methylation inhibitor and a histone methylation inhibitor are administered sequentially, they are separately formulated and can be provided in any order. When the DNA methylation inhibitor and a histone methylation inhibitor are administered simultaneously, however, they may be either separately formulated or combined in the same formulation. When combined in the same formulation, the DNA methylation inhibitor and the histone methylation inhibitor can be formulated so as to be released into the subject at the same time or at different times.

One embodiment described herein comprises, a method for administering a dosage form that provides a total amount of methylation inhibitor of about 1 to about 70 mg/m2/day, including all integers and fractions within the specified range.

In another embodiment described herein comprises a dosage of about 1 mg/m$^2$/day methylation inhibitor to about 70 mg/m$^2$/day methylation inhibitor, including all integers and fractions within the specified range. In another embodiment, the daily dosage is about 1 mg/m$^2$/day methylation inhibitor to about 65 mg/m$^2$/day methylation inhibitor, including all integers and fractions within the specified range. In another embodiment, the dosage is about 1 mg/m$^2$/day methylation inhibitor to about 60 mg/m$^2$/day methylation inhibitor, including all integers and fractions within the specified range. In another embodiment, the dosage is about 1 mg/m$^2$/day methylation inhibitor to about 55 mg/m$^2$/day methylation inhibitor, including all integers and fractions within the specified range. In another embodiment, the dosage is about 1 mg/m$^2$/day methylation inhibitor to about 50 mg/m$^2$/day methylation inhibitor, including all integers and fractions within the specified range. In another embodiment, the dosage is about 1 mg/m$^2$/day methylation inhibitor to about 45 mg/m$^2$/day methylation inhibitor, including all integers and fractions within the specified range. In another embodiment, the dosage is about 1 mg/m$^2$/day methylation inhibitor to about 40 mg/m$^2$/day methylation inhibitor, including all integers and fractions within the specified range. In another embodiment, the dosage is about 1 mg/m$^2$/day methylation inhibitor to about 35 mg/m$^2$/day methylation inhibitor, including all integers and fractions within the specified range. In one embodiment, the dosage is about 1 mg/m$^2$/day methylation inhibitor to about 30 mg/m$^2$/day methylation inhibitor, including all integers and fractions within the specified range. In another embodiment, the dosage is about 1 mg/m$^2$/day methylation inhibitor to about 25 mg/m$^2$/day methylation inhibitor, including all integers and fractions within the specified range. In another embodiment, the dosage is about 1 mg/m$^2$/day methylation inhibitor to about 20 mg/m$^2$/day methylation inhibitor, including all integers and fractions within the specified range. In another embodiment, the dosage is about 1 mg/m$^2$/day methylation inhibitor to about 15 mg/m$^2$/day methylation inhibitor, including all integers and fractions within the specified range. In another embodiment, the dosage is about 1 mg/m$^2$/day methylation inhibitor to about 13 mg/m$^2$/day methylation inhibitor, including all integers and fractions within the specified range. In another embodiment, the dosage is about 1 mg/m$^2$/day methylation inhibitor to about 11 mg/m$^2$/day methylation inhibitor, including all integers and fractions within the specified range. In another embodiment, the dosage is about 1 mg/m$^2$/day methylation inhibitor to about 10 mg/m$^2$/day methylation inhibitor, including all integers and fractions within the specified range. In another embodiment, the dosage is about 1 mg/m$^2$/day methylation inhibitor to about 9 mg/m$^2$/day methylation inhibitor, including all integers and fractions within the specified range. In another embodiment, the dosage is about 1 mg/m2 methylation inhibitor to about 8 mg/m$^2$/day methylation inhibitor, including all integers and fractions within the specified range. In another embodiment, the dosage is about 1 mg/m$^2$/day methylation inhibitor to about 7.5 mg/m$^2$/day methylation inhibitor, including all integers and fractions within the specified range. In another embodiment, the dosage is about 1 mg/m$^2$/day methylation inhibitor to about 7 mg/m$^2$/day methylation inhibitor, including all integers and fractions within the specified range. In another embodiment, the dosage is about 1 mg/m$^2$/day methylation inhibitor to about 6.5 mg/m$^2$/day methylation inhibitor, including all integers and fractions within the specified range. In another embodiment, the dosage is about 1 mg/m$^2$/day methylation inhibitor to about 6 mg/m$^2$/day methylation inhibitor, including all integers and fractions within the specified range. In another embodiment, the dosage is about 1 mg/m$^2$/day methylation inhibitor to about 5.5 mg/m$^2$/day methylation inhibitor, including all integers and fractions within the specified range. In another embodiment, the dosage is about 1 mg/m$^2$/day methylation inhibitor to about 5 mg/m$^2$/day methylation inhibitor, including all integers and fractions within the specified range. In another embodiment, the dosage is about 1 mg/m$^2$/day methylation inhibitor to about 4.5 mg/m$^2$/day methylation inhibitor, including all integers and fractions within the specified range. In another embodiment, the dosage is about 1 mg/m$^2$/day methylation inhibitor to about 4 mg/m$^2$/day methylation inhibitor, including all integers and fractions within the specified range. In another embodiment, the dosage is about 1 mg/m$^2$/day methylation inhibitor to about 3.5 mg/m$^2$/day methylation inhibitor, including all integers and fractions within the specified range. In another embodiment, the dosage is about 1 mg/m$^2$/day methylation inhibitor to about 3 mg/m$^2$/day methylation inhibitor, including all integers and fractions within the specified range. In another embodiment, the dosage is about 1 mg/m$^2$/day methylation inhibitor to about 2.5 mg/m$^2$/day methylation inhibitor, including all integers and fractions within the specified range. In another embodiment, the dosage is about 1 mg/m$^2$/day methylation inhibitor to about 2 mg/m$^2$/day methylation inhibitor, including all integers and fractions within the specified range. In another embodiment, the dosage is about 1 mg/m$^2$/day methylation inhibitor to about 1.5 mg/m$^2$/day methylation inhibitor, including all integers and fractions within the specified range. In another embodiment, the dosage is about 1 mg/m$^2$/day methylation inhibitor. The total dose may be administered in any number of individual dosage forms that cumulatively total the dose. Other dosages are also possible.

Materials and Methods

Mice: Retired breeder female BALB/c mice were purchased from the National Cancer Institute (NCI) and were used for the generation of cartilage proteoglycan-induced arthritis (PGIA). Briefly, the mice were immunized with PG purified from knee joint cartilage osteoarthritis patients who had undergone joint replacement surgery. PG was injected intraperitoneally (IP) 3 times (at 3-week intervals, 100 μg PG core protein/injection) with 2 mg of dimethyl-dioctadecyl-ammonium bromide adjuvant into BALB/c mice. Mice with acute arthritis were sacrificed 9 days after the 3rd PG immunization. Animal experiments were approved by the Institutional Animal Care and Use Committee at Rush University Medical Center, Chicago, Ill. PGIA is the only murine arthritis model that has both IgG- and IgM-type RFs and anti-citrullinated cyclic peptide antibodies (ACPA), which are predictive markers of disease development both in this model and RA. Additional characteristics of RA are also present in other rodent models, but the above listed phenotypes and genotypes are present together only in PGIA. Therefore, PGIA exhibits the highest similarities to RA among the various induced autoimmune murine models of arthritis and provide a valuable tool for exploring arthritis-related epigenetic events.

Drug treatment and scoring of arthritic mice: Drugs that prove to be the most effective in ex vivo experiments will be tested on mice with established arthritis will be tested (Table 1). Arthritic mice will be treated with one of the DNA methyltransferase inhibitors via intraperitoneal injection (i.p.) at three various doses daily for 14 days. The other group of PGIA mice were treated with one of the histone-modifying enzyme inhibitors at three various doses for 14 days. This drug will also administered by daily i.p. Control mice will be treated with "placebo" (carrier of the tested drug, most probably DMSO). Paws of mice, including the ankle and wrist joints, will be inspected for signs of arthritis (swelling and redness) every second day. The degree of arthritis will be scored visually on a scale of 0 to 4 for each paw (0—no swelling or redness; 1—mild swelling/redness; 2—moderate swelling of the entire paw, including the ankle; 3—severe swelling; 4—severe swelling with hardening of the periarticular soft tissue). Effectiveness of treatments will be expressed as a sum of inflammation scores (0 to 16 per mouse). In addition, measurements of ankle and wrist joints will be performed with minicaliper to gain quantitative data regarding effects of the applied treatments. At the end of experimental period mice will be euthanized and spleen will be removed for further analysis including genomic DNA, total RNA and protein lysate preparation.

TABLE 1

Treatment of arthritic animals with epigenetic enzyme inhibitors.

| Experimental groups | | | Mice |
|---|---|---|---|
| Targeted inhibition of | DNA methyl. | Ctrls | 15 |
| | | Low dose | 15 |
| | | Medium dose | 15 |
| | | High dose | 15 |
| | | Sub-total: | 60 |
| | Histone modif. | Ctrls | 15 |
| | | Low dose | 15 |
| | | Medium dose | 15 |
| | | High dose | 15 |
| | | Sub-total: | 60 |
| | Both | Ctrls | 15 |
| | | Low dose | 15 |
| | | Medium dose | 15 |
| | | High dose | 15 |
| | | Sub-total: | 60 |
| | | Total: | 180 |

PGIA mice will be treated as described above with DNA methylation inhibtors, histone methylation inhibitors and combinations of DNA and histone methylation inhibitors and scored as described above. Dosing ranges for each group will be administered and scored.

Human subjects: Human studies were approved by the Institutional Review Board (IRB) at Rush University Medical Center. All patients and control individuals were recruited under an IRB-approved protocol and gave informed consent.

Cell cultures: A20 mouse B cell line were purchased from American Type Culture Collection (ATCC) and were maintained at 37° C. in a 5% CO2-humidified atmosphere on Dulbecco's modified Eagle's medium (DMEM) containing 10% fetal bovine serum (FBS) and 100 ng/ml each of penicillin and streptomycin. Human B cell line GM12878 were purchased from ATCC and cultured in RPMI 1640 media and maintained at 37° C. in a 5% CO2-humidified incubator as described above.

Azacitidine (AzaC) treatment of A20 cells: 105 cells were seeded into 6-well plates containing 3 ml cell culture medium. Before AzaC treatment, cells were incubated for 16-18 hours at 37° C. in 5% CO2. Cells were treated with AzaC to a final concentration of 5, 10 and 150¢, control cells were treated with 0.15% DMSO. Cells were incubated for 48, 72 and 96 hours under standard cell culture conditions. After 48 and 72 hours AzaC was replenished to keep the desired AzaC concentration. Harvested cells were washed with phosphate buffered saline (PBS) and viability and cell numbers were assessed on Vi-cell XR cell counter (Beckmann Counter).

RNA isolation, cDNA synthesis, and quantitative reverse transcription-polymerase chain reaction (qRT-PCR): Total RNA from cell culture was isolated using QIAmp RNA Blood Kit (Qiagen) or Direct-Zol™ RNA miniprep Kit (Zymo Research). Each RNA sample was digested with 4U of TurboDNase™ (Ambion) and purified with RNA clean and concentrator-5 (Zymo Research) and samples quantified using NanoDrop 1000 spectrophotometer. Primary mouse cells were collected from the spleens, on day 9 after the third PG injection. B cells were purified using antibody-coated magnetic beads (StemCell Technologies). RNA was isolated from purified mouse lymphocytes using a TRI reagent (Sigma-Aldrich) immediately after separation.

Human peripheral blood mononuclear cells (PBMCs) were separated on a Ficoll gradient from blood samples obtained from consenting, healthy individuals and from RA patients naive to treatment with disease-modifying antirheumatic drugs (DMARDs). The isolated mononuclear cells were stored in RNAlater (Life Technologies) until RNA preparation. Complementary DNA was reverse transcribed from 1 µg total RNA with iScript™ Reverse Transcription Supermix (Bio-Rad Laboratories). Quantitative RT-PCR (CFX Connect™, Bio-Rad Laboratories) was performed in triplicate using SsoAdvanced™ Universal SYBR Green Supermix (Bio-Rad Laboratories) in 10 µl. Quantitative RT-PCR was performed using CFX machine (Bio-Rad). Primers were designed using PrimerQuest software and were manufactured by Integrated DNA Technologies. The qRT-PCR primer sequences are available upon request from the corresponding author. The specificity of the qRT-PCR product was monitored by a post-PCR melting curve analysis. Samples were tested in duplicate, and the CFX manager software was used to calculate the normalized fold expression changes based on the ΔΔCt method. Measured Ct values were normalized to β-actin internal control values.

Genomic DNA (gDNA) purification, Global DNA methylation assessment and Methylated CpG island ecovery assay (MIRA)-assisted microarray (MIRA-chip) and data analysis: gDNA was isolated from affinity purified B cells using QIAamp DNA Mini Kit (Qiagen). Global DNA methylation analysis was performed using Imprint Methylated DNA Quantification kit (Sigma-Aldrich). Experiments were conducted according to manufacturer instructions MIRA enrichment of methylated gDNA fractions were performed by MethylCollector™ Ultra kit (Active Motif), captured fractions were labeled and hybridized to microarrays harboring all mouse promoters and CpG island outside of the promoter regions (NimbleGene). Data analysis was performed as described before.

Electrophoretic Mobility Shift Assay (EMSA): Protein-DNA interaction studies were performed with Gelshift™ Chemiluminescent EMSA Assay Kit (Active Motif). Biotin-labeled oligonucleotides were used in binding reactions and signal detection was carried out according to the company provided protocol. Oligonucleotide sequences used in EMSA's are available upon request.

Chromatin immunoprecipitation (ChIP): ChIP-IT® PBMC Kit (Active Motif) was used for in vivo detection of transcription factor binding to the investigated promoters. PCR primers used in ChIPs are available upon request.

Western blot analyses: AzaC treated A20 cells (10 µM AzaC for 72 hours) washed with PBS, nuclear and cytoplasmic extracts were prepared from $8\times10^6$ cells using Nuclei EZ Prep kit (Sigma-Aldrich) according to the manufacturer's protocol. Protein extracts were separated on a 4-10% SDS-polyacrylamide gel (Bio-Rad Laboratories) and blotted onto Immuno-Blot membrane (Bio-Rad Laboratories). Western blots were serially probed with anti-AhR, anti-Lamin-B1 and glyceraldehyde-3-phosphate dehydrogenase (GAPDH) (Santa Cruz Biotechnologies) antibodies. ECL Western Blotting Substrate (ThermoScientific) was used for detection.

Results

Arthritis-Specific DNA Methylation Events in B Cells of Mice with PGIA

Figure 1C:
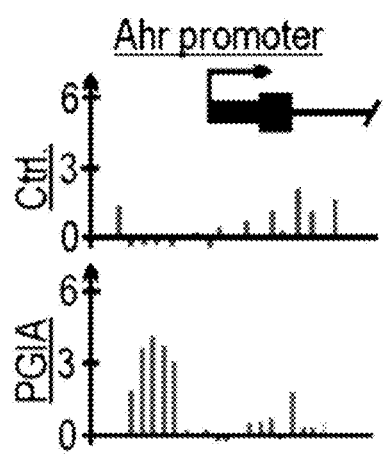
Figure 1D:
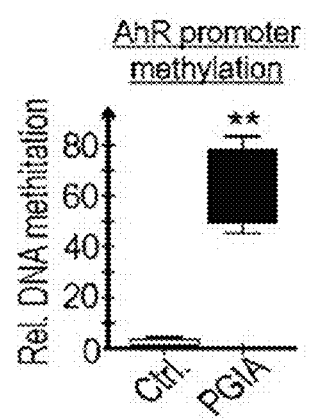
Figure 1E:
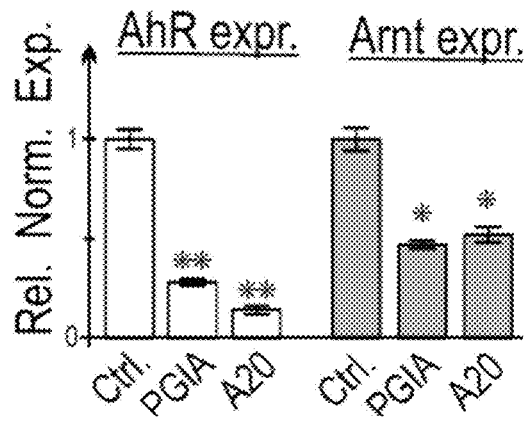
Figure 1F:
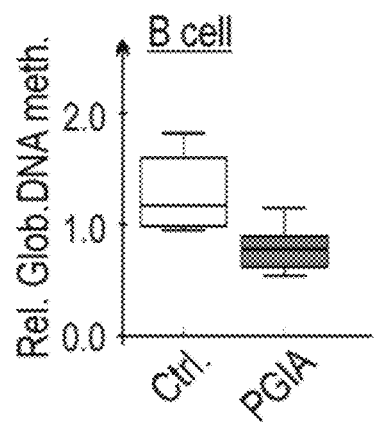

As a first step, to explore disease-associated DNA methylation changes, global DNA methylation was assessed using methylated DNA-specific ELISA (FIG. 1(F)). Global DNA methylation level was at least 20-25% lower in genomic DNA samples isolated from arthritic B cells (FIG. 1(F)). Next, DNA demethylation catalyzing ten-eleven translocation 1 (Tet1), Tet2 and Tet3 enzymes show increased expression in arthritic samples was investigated, which could explain the observed global demethylation. Some increase in the expression of Tet enzymes was detected but it was not statistically significant (data not shown). After detecting significant global methylation, identification of those gene promoters that underwent arthritis-specific DNA methylation changes during development of PGIA was undertaken. All mouse promoters (~25,000) were investigated around the transcription start site (700 bps upstream and 300 bps downstream), and several hundreds of promoters were "arthritis specifically" methylated using MIRA-chip method (FIG. 1(A). Reliability of the MIRA-chip data was tested and approved by CXXC-method (FIG. 1(N)). In accordance with ELISA data, a dominantly hypomethylation event could be detected in arthritic mouse B cells (Not shown). The majority of differentially methylated regions (DMR) located in CpG shores (i.e, flanking regions of CpG islands) and promoters with low CpG content. The less but more characteristic hypermethylation showing DMRs were mainly associated with core promoter regions suggesting more severe effect of gene expression. Subsequent studies were focused on a hypermethylated DNR that occurred in a promoter that regulates the expression of a broad-effect transcription factor.

Epigenetic Marks, Such as DNA Methylation and Histone Modifications, Determine Gene Expression Patterns of Cells, and Impairment of Epigenetic Mechanisms Induce Changes that Lead to Disease Formation.

In one embodiment described herein, epigenetic markers, such as DNA methylation and histone modifications determine gene expression patterns of cells, impairment of epigenetic mechanisms that induce changes leading to disease formation. Genome-wide DNA methylation studies were conducted in mice with proteoglycan (PG)-induced arthritis (PGIA), a murine model of RA. These studies identified a set of genes that have undergone epigenetic changes in an arthritis-specific manner. Hypermethylation in the promoter region of a transcription factor-encoding gene ("aryl hydrocarbon receptor" [AhR]) resulted in significant downregulation of AhR expression in the B cells of arthritic mice, and insufficient expression of this transcription factor was also observed in the peripheral blood mononuclear cells (PBMCs) of RA patients. In addition, the "aryl hydrocarbon receptor nuclear translocator" (Arnt)-coding gene, which is responsible for transferring AhR into the nucleus, was also downregulated in arthritic samples, suggesting that the pathway dedicated to suppressing antibody production is damaged at multiple points in RA. AhR and Arnt genes were focused on for further analyses because; (i) experimental evidence indicates that their promoters are silenced by histone and DNA modifications, and (ii) both encoded proteins play roles in the regulation of other genes and, either directly or indirectly, control regulatory T cell (Treg) cell development and inhibit antibody production in B cells. Epigenetic alterations, which affect a critical transcription factor in immune cells, trigger widespread changes in the network of interacting genes.

DNA Hypermethylation in AhR Promoter Triggers Gene Silencing in Arthritic Mouse B Cells.

MIRA-chip analysis revealed differential DNA methylation in the 5' promoter region of mouse AhR gene (FIG. 1(C)). The presence of AhR promoter-linked epimutation was verified in three independent arthritic and control samples by microarray, and proved to be statistically highly significant in B cells (FIG. 1(D)). Next, we investigated how this epimutation affects gene expression. RNA was isolated from arthritic and control B and T cells, qRT-PCR was used to evaluate the cell-specificity of the altered gene expression. Indeed, as DNA methylation studies suggested, the downregulated expression of AhR was exclusive to arthritic B cells (FIG. 1(E)). Interestingly, de novo disease-linked DNA methylation events could not be detected in the Arnt promoter region, suggesting that other types of repressive epigenetic marks must contribute to its reduced expression. In arthritic T cells, altered expressions of AhR and Arnt genes was observed but changes were not statistically significant (data not shown). Therefore, subsequent preliminary experiments were conducted on the A20 B cell line.

Treatment of A20 Cells with DNA Methyltransferase-Specific Inhibitor can Reactivate the Expression of AhR and a Few Inflammation-Related Genes.

To provide further evidence that DNA methylation is the responsible factor for the silenced state of AhR gene, DNA methyltransferase inhibitor Azacitidine (AzaC); an FDA-approved drug for cancer treatment was used. The effect of AzaC was investigated in A20 cells, a BALB/c B cell lymphoma cell line, in which AhR gene promoter was similarly hypermethylated and its expression downregulated as described in arthritic mouse B cells (FIG. 1(E)). AzaC was added in various concentrations to A20 cell cultures and followed its effect on AhR expression by qRT-PCR for three days (FIG. 1(L)). AzaC treatment could revive AhR expression after two days even when the inhibitor was employed at low concentration (FIG. 1(L)). Parallel with the induced (re)expression of AhR gene elevated AhR protein level was not detected with Western blotting. Interestingly, AhR translocated into the nucleus without adding specific agonist to A20 cultures (FIG. 1(K)). Next, the question whether translocated AhR could be transcriptionally active and whether it could promote the expression of targeted genes was investigated. Therefore, the expression of Cyp1a1 gene was monitored, which is a well-known target of AhR. For Cyp1a1 activation, reactivation of Arnt transcription factor is essential, which is similarly silenced as is the AhR gene in both arthritic B cells and A20 cells (FIG. 1(E)). Although arthritis-linked DNA methylation could not be detected in Arnt promoter it was reactivated after AzaC treatment. These data imply that functional reactivation of AhR is possible by DNA methyltransferase specific inhibitor (FIG. 1(M)).

Figure 3A:
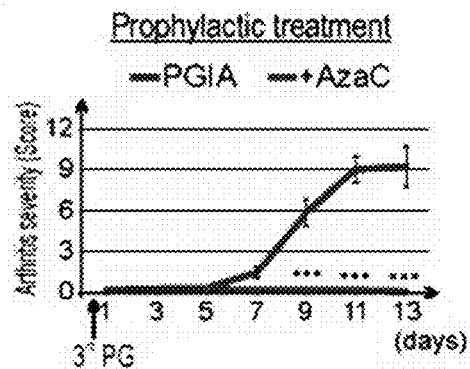
FIGS. 3A-J illustrate that AzaC-treatment reactivates Ahr expression in vivo and prevents PGIA development in mice. Female BALB/c mice were immunized with human cartilage PG (three-times at three 3-week intervals). Limbs were inspected regularly after the second PG injection for signs of arthritis (redness and swelling) and visual arthritis score was assigned to all paws as described in methods.
Figure 3B:
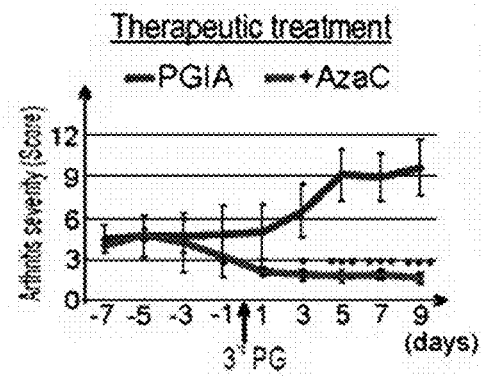
Figure 5A:
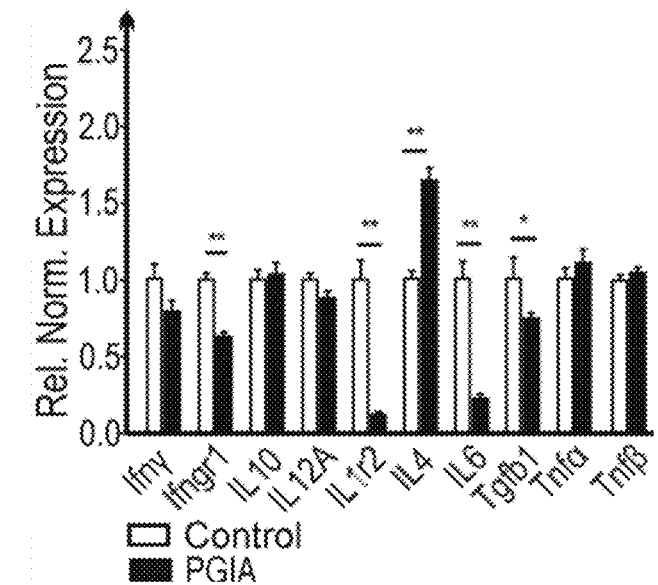
FIGS. 5A-C depict cytokine and immunoglobulin gene expression changes in arthritic B cells and A20 cell line.
Figure 5B:
Figure 5C:
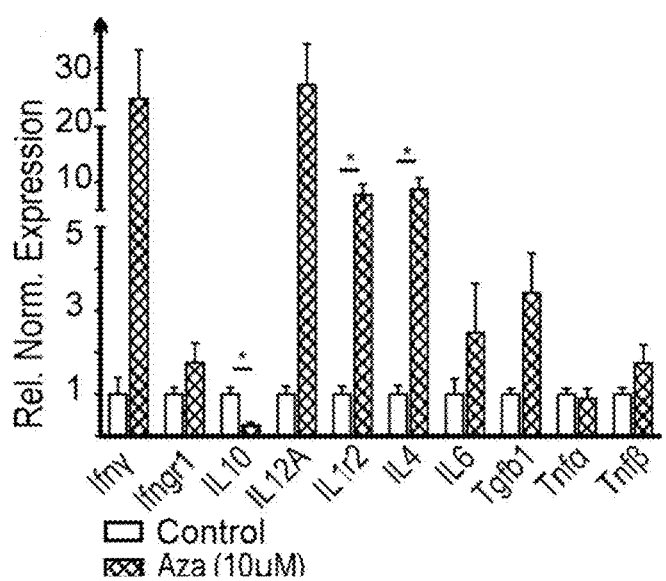

Arnt is not the only partner of AhR in transcriptional regulation; it can also form heterodimers with RelA and RelB transcription factors and recognize characteristic DNA motives in the genome. Using these DNA binding motif sequences, pro- and anti-inflammatory gene promoters were screened to identify tentative targets for AhR. A promoter database search revealed 10 potential targets for AhR and its interacting cofactors. To this end, whether AzaC treatment-mediated AhR reactivation can induce gene expression changes for the tentative target genes in A20 cells (FIG. 5) was investigated, which could explain the behavior of differentially expressed cytokine and immune globulin genes in arthritic B cells (FIGS. 3A and 3B). It was found that reactivation of AhR expression could significantly alter the expression of three tentative AhR target genes (FIG. 5(C)), and may provide a reasonable answer as to how and the mechanism involved in the downregulated expression of Illr2 gene in arthritic B cells.

In addition to promoter sequences located close to transcription start sites, distant regulatory regions were inspected for the presence of putative AhR binding sites. Such distant enhancers that had been known for playing a role in regulation of inflammation and/or immune response regulated genes were studied.

One of these enhancers was the immunoglobulin heavy chain 3' regulatory region (3'IghRR), which is essential for immunoglobulin heavy chain maturation and expression. Using the open-access database JASPAR for the prediction of transcription factor binding sites, we detected multiple tentative sites for AhR binding in 3'IghRR. In fact, a recent study demonstrated that AhR is a dominant negative regulator of 3'IghRR mediated activation in B cells. Since the autoantibody production is the most appreciated function of B cells in RA pathogenesis, we investigated whether reactivation of AhR by AzaC can suppress antibody production in primary arthritic B cells. It is known that IgA, IgE, and IgG1 gene expression is supervised by 3'IghRR in B cells; therefore, expression of these genes in arthritic samples was checked. IgG1 expression is significantly upregulated in B cells isolated from mice with PGIA (FIG. 5(B)), but not in A20 B cell line.

RA-Associated DNA Methylation of a Distant Regulatory Element May Suppress AHR Gene Expression in Human PBMCs.

Animal studies provided a basis for the investigation of AhR gene expression in human arthritic samples. Because RA therapies can significantly influence gene expression profiles, AhR expression was studied in PBMCs isolated from un-treated (i.e., DMARD-naive) RA patients and control individuals. Quantitative gene expression analysis revealed that AhR expression was significantly downregulated in RA samples (FIG. 1(G)) but disease-associated DNA methylation (i.e., hypermethylation) could not be detected in the close proximity of AhR promoter (data not shown). To explore RA-specific methylation harboring region(s) that might be responsible for silencing of AhR gene, the search was extended to distant upstream regulatory regions. CpG dinucleotide carrying loci that popped up in the ENCODE database as 'DNase I hypersensitivity regions' (DNHRs) and were hot spots for transcription factors binding in ENCODE ChIP-seq databases were focused on. Four distant sequences were analyzed (FIG. 1(D)) with MIRA, a region which was differentially methylated in DMARD-naive RA patients compared to control subjects (FIG. 1(H)) was found. Differentially methylated region C (DMR-C) harbors tentative binding sites for transcription factors that are known to be implicated in B cell development such as NFkB1, homeobox A5 (HOXA5), myeloid zinc finger 1 (MZF1) and Spi-B transcription factor (SPIB). This set of transcription factors and the observed de novo DNA hypermethylation imply that a differentially methylated B cell-specific enhancer can also be involved in RA pathogenesis.

Discussion

Antibody production and inflammatory cytokine expression create the essence of humoral immunity, a highly organized system which can turn against its own body's components in autoimmune diseases. The dysregulation of humoral immunity can originate in either genetic mutations or epigenetic alterations, and these disease-specific changes are less understood than those associated with altered cytokine or antibody expression. The relationship between epimutations and the observed gene expression changes is mostly not evident, it is still not clear whether they are causative agents (drive mutations) or just by-products of pathogenesis (passenger mutations). Several hundreds of arthritis-specific DNA methylation changes were detected in mouse B cell epigenome (FIG. 1(A), but it is implausible that all of these methylation changes are actively involved in pathogenesis. Rather, many of them are consequences of dysregulated activity of DNA methyltransferases or enzymes with DNA demethylase activity (i.e., Tet enzymes). The real challenge is to pinpoint those epimutations that play role in the initiation and/or progression of arthritis. To this end, gene expression analysis around the epimutation can be a reasonable approach. qRT-PCR studies revealed that most of the de novo DNA methylation events at CpG island shores do not affect expression of the neighboring genes (data not shown), and in this sense they are passenger mutations. This study was mainly focused on the analysis of the AhR gene that carries a characteristic hypermethylated DMR in its promoter, which is accompanied by gene silencing in arthritic mouse B cells (FIGS. 1(C) and (E)). DNA methylation-mediated AhR silencing can have a profound effect on the whole transcriptome, because, as a transcription factor, it regulates all kinds of target genes including metabolic enzymes, transcription regulators and immunity related mediators. What makes the picture more complex is that depending on the interacting partner AhR can behave either as a transcriptional activator or repressor. Evidence that reactivation of the silent AhR gene affects the expression of several arthritis-associated expression showing cytokines is presented (FIGS. 5(A and (B). AzaC treatment-induced activations or repressions mediated by AhR were not always statistically significant, which can be explained by the fact that gene-specific activation (or silencing) is not a single factor conducted process and cofactors may have not been present. For example, Arnt—the best-characterized interacting partner of AhR, is also silenced in arthritic B cells, but just prolonged and high concentration AzaC treatment could have released it from the silent state (FIG. 1(M)).

Previously, AhR binding to the transcriptional regulatory region of Igh locus has been demonstrated in a permanent B cell line carrying a special reporter gene mini locus driven by 3'IghRR. Both in vitro (i.e., EMSA) and ex vivo (i.e., ChIP) studies were conducted, that clearly demonstrate the AhR's ability to bind directly to 3'IghRR. Indeed, 3'IghRR is a transcriptional enhancer that behaves as a silencer after binding of AhR. AhR possesses E3 ubiquitin ligase activity and can promote selective degradation of estrogen receptors (ERα and ERβ) and androgen receptor (AR). Therefore, it is plausible to suppose that AhR can also promote degradation of NFκB that can also bind to 3'IghRR and otherwise it would activate Igh locus located genes.

Quantitative gene expression studies performed on reasonable number of control (n=17) and DMARD-naive RA samples (n=47) proved that AhR is similarly downregulated in human samples (i.e., PBMCs) as in mouse arthritic B cells. These data suggest the presence of a common AhR-related gene regulatory mechanism, which is responsible for supervising of immunoglobulin expression, and this gene cascade is disturbed in arthritis by de novo DNA hypermethylation. The human DMR is located upstream, but close proximity to the AhR promoter, which location is different than seen in mice. Similar distant DNA methylation sensitive enhancer has been already described that governs FOXP3 expression in Tregcells. It is also demonstrated regarding this FOXP3 enhancer that methotrexate treatment could result in DNA demethylation that can lead to reactivation of Treg cell function in RA. Functional analysis including transient expression studies and identification of transcription factors of this AhR-related distant regulatory element is the subject of ongoing studies.

Although a clear connection between epigenetic alteration and gene expression changes was observed (i.e., de novo DNA methylation→AhR downregulation→IgG1 overexpression), it is still an open question what the very first act/reason is for inappropriate methylation of AhR promoter in the context of arthritis. This is not a new question regarding DNA methylation-prone vs. -resistant promoters since cancer research has been struggling with it for years. This issue as to how genetic mutations or just simple polymorphisms are able to define epigenetic profiles or, vice versa, how epigenetic events contribute to promotion of genetic polymorphisms needs to be investigated.

Findings discussed here demonstrate that targeted inhibition of DNA methyltransferase can restore AhR expression and suppress antibody production in tissue cultures can be indicative and encouraging for testing these kinds of drugs in animal models of RA.

Another embodiment described herein is directed to the characterization of repressive epigenetic signals and testing of enzyme blockers in arthritic B cells. Proof-of-principle experiments reveal that AhR and Arnt genes are epigenetically silenced in the mouse B cell line (A20) but that their expression can be revitalized with epigenetic enzyme inhibitors. Preliminary A20 cell-related data in ex vivo cultured mouse B cells will be evaluated and then existing epigenetic landscape of these two promoters in B cells isolated from arthritic mice will be characterized. Next, in light of these epigenetic profiling data, appropriate epigenetic enzyme inhibitors will be chosen to investigate whether transcriptional blockage of the promoters can be suspended using single enzymes or enzyme inhibitor cocktails. Techniques that are suitable for (i) exploring the epigenetic architecture of AhR and Arnt promoters in isolated B cells (i.e., MIRA and ChIP-PCR) and (ii) detecting restored gene expression (i.e., quantitative real-time RT-PCR [qRT-PCR]) will be employed. ELISPOT (Enzyme-Linked ImmunoSpot) analyses will be performed to investigate whether the targeted drug treatments are able to suppress antibody production. These studies will provide information regarding the behavior of ex vivo cultured B lymphocytes to specific enzyme inhibitors, the results will inform also animal studies.

One embodiment described herein targets epigenetic factors with therapeutic agents. Epigenetic factors identified herein are enzymes with well-defined catalytic activities which render them suitable for potential drug targets. Current RA therapies mainly employ small-molecule drugs in monotherapy or in combination with rationally designed cytokine neutralizing antibodies. The molecular targets of the current small-molecule drugs have been extensively investigated, but none of them have been proven to act directly on epigenetic enzymes. Genome-wide DNA methylation and accompanying gene expression profiles in PG-induced arthritis, a progressive autoimmune model of RA was studied to determine the therapeutic potential of epigenetically altered genes. A group of differentially methylated genes were identified in B cells of arthritic mice, including the DNA methylation-silenced Ahr, which encodes a versatile transcription factor implicated in immune cell differentiation.

In another embodiment described herein, therapeutic effects of epigenetic enzyme inhibitors will be explored in PGIA mice. Inhibition of AhR gene expression can be relieved in mouse B cell lines by deploying specific enzyme inhibitors. Therefore, the ability of drugs based on epigenetic enzyme inhibitors to cure established arthritis will be investigated. This will enable the selection of the most effective drug(s) or drug combinations for animal studies. After the first sign of arthritis, multiple doses of the drug(s) will be employed. The effects of these drugs on arthritic paws and joints will be monitored during the treatment period and compared to a control (vehicle) group of animals.

In another embodiment described herein, DNA methylation-targeting drug is shown to have a therapeutic effect in treating PG-induced arthritic mice/animals with AzaC, a DNA methylation inhibitor. Administration of AzaC restored Ahr expression with beneficial effects on arthritis. The Ahr gene was reactivated in AzaC-treated PG-induced arthritic mice/animals, and the clinical symptoms of RA were abolished. This is the first example showing that a DNA methylation-targeting drug has therapeutic potential in the treatment of RA.

In another embodiment, it will be illustrated that AzaC and other drugs with similar action spectra (i.e., targeting epigenetic enzymes) provide a new concept for RA therapy. Epigenetic alterations resulting in DNA and histone methylation that take place in B cells are critical factors in arthritis pathogenesis and are targets of therapeutic drug treatments as disclosed in this embodiment. AzaC is an FDA-approved anti-cancer drug but, in its effective dose, induces severe adverse drug events (ADEs) in cancer patients. The goal of the treatment is to avoid or minimize ADEs in RA therapy which was achieved either by lowering the employed doses or by employing new epigenetic blockers with different modes of action. In this embodiment, a histone methylation inhibitor acting either singly or in concert with DNA methylation will be used to achieve gene silencing in animal models of RA.

Characterization of DNA Methyltransferase Inhibitors in Mice with PG-Induced Arthritis.

AzaC-mediated blocking of DNA methylation has a beneficial effect in treating PG-induced arthritis. Arthritic mice tolerated AzaC at the applied dose, but the lowest effective dose beneficial in maintaining prolonged treatment without side effects will be determined. RA is a complex disease, in addition, the patient population is very heterogeneous implying that therapeutic agents are usually effective on specific subsets of patients, and drug responsiveness can be quite different. To that effect, a broader range of therapeutic options will be evaluated by investigating multiple DNA methyltransferase inhibitors with different modes of action.

Exploration of the Therapeutic Potential of Histone Methyltransferase Inhibitors in Mice.

Ezh2 is a highly specific histone methyltransferase, which was upregulated in arthritic B cells and involved in the promotion of DNA methylation-mediated gene silencing. Ezh2 is strontly linked to RA because one of its interacting partners Phf19 is a significant RA risk factor identified by genome-wide associated studies (GWASs). The mechanism by which Phf19/Ezh2-silenced genes in B cells contribute to arthritis, and Ezh2-specific blockers will also be evaluated in therapeutic experiments. Furthermore, whether combined treatments with DNA and histone methyltransferase inhibitors are more effective than their separate application in arthritic animals will be determined.

Epigenetic and Gene Expression Profile Mapping in RA Patients.

Methylation targeting drugs will be considered as plausible candidates in RA therapy by delineating the mechanisms of arthritis pathogenesis in mouse and human B cells which are similar or even identical for some druggable genes. DNA methylation and gene expression alterations in B cells isolated from control subjects and RA patients will be determined. B cell-specific human and mouse data sets will be compared to identify common arthritis-associated genes, which will lead to a strong support to accepting methylation blockers as promising arthritis therapeutics.

Epigenetic Factors as Potential Druggable Targets for Arthritis Therapy.

In another embodiment, the potential for epigenetic factors as potential druggable targets for RA therapy will be demonstrated. Although over a hundred arthritis risk loci have been mapped by GWASs, studies in monzygotic twins show that the role of genetic factors in RA pathogenesis is low, therefore epigenetic factors were investigated for their potential in targeted treatment of RA. Epigenetic enzymes are able to deposit, interpret and eliminate epigenetic signals and establish a proper nuclear milieu for cell-specific gene expression by defining which sets of genes are turned on and which ones are turned off. Accordingly, erroneous epigenetic mechanisms result in the miswriting, misreading or faulty removal of gene expression-defining information that can lead to disease.

DNA methylation and histone methylation are two major components of the epigenome and act together to control cell-specific gene expression at an appropriate time frame or at an optimal time point. DNA methylation is catalyzed by DNA methyltransferases (DNMTs) and is associated with transcriptional repression and gene silencing in the context of promoters. Historically, DNA methylation was the first epigenetic alteration implicated in RA. Currently, there are two FDA-approved DNA methylation inhibitors, AzaC and the chemically related 5-aza-2'-deoxycytidine (dAzaC), these two methylation inhibitors are employed in cancer therapy. Both agents, AzaC and dAzaC are incorporated into replicating DNA and covalently capture DNMT. The potential for new DNMT inhibitors, in addition to AzaC and dAzaC as effective therapeutic agents for RA treatment and prophylaxis will be investigated.

In another embodiment, epigenetic modifications that occur on histone proteins and either promote or silences transcription of neighboring genes will be explored. Histone methylations will be evaluated, more specifically those that occur at the 27th lysine residue in histone H3 molecules with tri-methylation (frequently abbreviated as H3K27me3) catalyzed by the Ezh2 enzyme. Hereafter, H3K27me3 will be referred to as "histone methylation." The term histone methylation includes other types of histone methylation and is not limited to H3K27me3. This type of histone methylation, similar to DNA methylation, is associated with gene silencing by generating an epigenetic milieu around promoters that prevents the effective initiation of gene transcription. Mechanistically, Ezh2-catalyzed histone methylation precedes DNA methylation and marks genes for subsequent DNA methylation. Ezh2 can directly interact with DNMTs and recruits them to particular genes.

Figure 6:
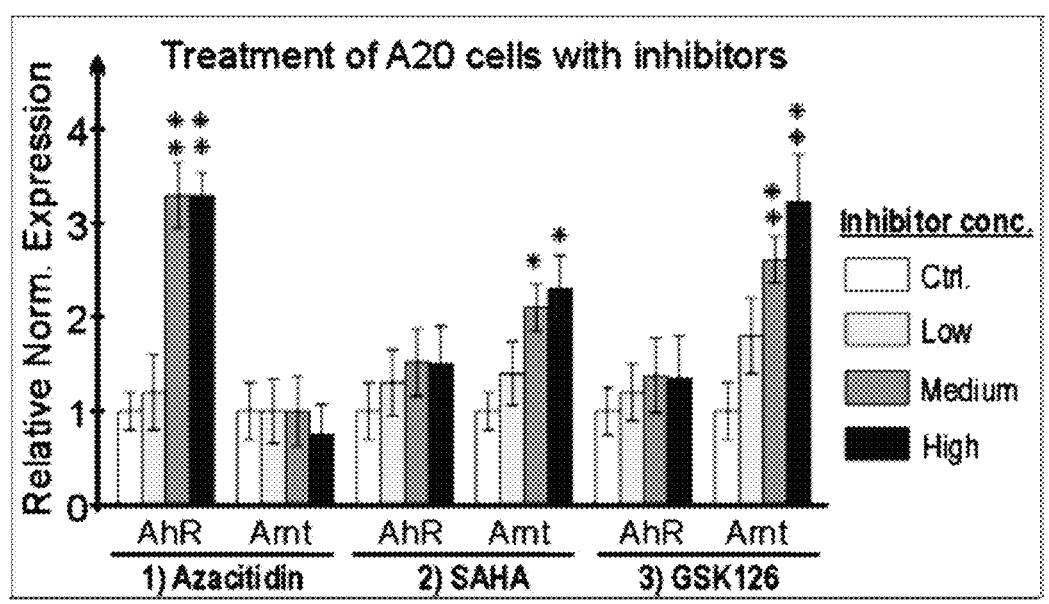
FIG. 6 depicts findings of testing of epigenetic enzyme inhibitors in cell culture. A20 cells were cultured in the presence of enzyme blockers for 72 hours and gene expression was monitored by qRT-PCR. (1) Inhibition of DNA methyltransferases with 2, 5 and 10 µM of AzaC; (2) HDAC inhibition with 0.1, 0.5 and 1.0 µM of SAHA; and (3) Blocking of Ezh2 methyltransferase activity with 5, 10 and 15 µM of GSK126. All control cultures were mock treated with DMSO. *P-value≤0.05, **P-value 0.01.

In an embodiment described herein, targeted inhibition of epigenetic enzymes involved in repression of gene expression is demonstrated. Both AhR and Arnt genes downregulate expression in mouse A20 cells, which is similar to levels detected in arthritic B cells (FIG. 1(E)). Therefore, this B cell line was chosen to investigate whether the suppressed expression of these genes could be released or weakened with epigenetic enzyme inhibitors. AhR promoter was found to be de novo methylated in arthritic B cells. This region was an obvious choice for testing a DNA methyltransferase inhibitor. Azacitidine was used, which is an FDA approved chemo-therapeutic agent for cancer and a nucleoside analogue of cytidine that incorporates into DNA and leads to the covalent binding (i.e., trapping) of DNA methyltransferase and subsequent blocking of its action. It was found that AzaC treatment of A20 cells caused significant reactivation of AhR gene expression in the presence of 5 and 10 µM of inhibitor (FIG. 6-1). AzaC treatment could not trigger significant upregulation of Arnt gene expression (FIG. 6-1), which is in accordance with our DNA methylation data because its promoter was not de novo methylated in arthritic B cells.

Another embodiment described herein is directed to the testing of epigenetic enzyme inhibitors in cell cultures. A20 cells were cultured in the presence of enzyme blockers for 72 hours and gene expression was monitored by qRT-PCR. (FIG. 6 (1-3)). To, Two enzyme inhibitors were tried to release the transcriptional blockage of the Arnt promoter. First, suberanilohydroxamic acid (SAHA, an FDA approved histone deacet (HDAC) inhibitor for cutaneous T-cell lymphoma) was tested because transcriptionally silent genes are always hypoacetylated at their promoter regions and HDACs catalyze acetyl-group removal. SAHA treatment could increase the gene expression from both genes (i.e., AhR and Arnt) without high cytotoxicity (FIG. 6(2)). Reactivation of the AhR gene (i.e., after SAHA treatment) is not surprising because DNA methylation and histone deacetylation usually act in concert, leading to stably downregulated gene expression. Next, GSK126, a selective small-molecule inhibitor of EZH2 methyltransferase was tested, because trimethylation of lysine 27 in the histone H3 molecule is a strong epigenetic repressor signal and is implicated in B cell development; EZH2 methyltransferase catalyzes this signal. Treatment of A20 cells with GSK126 promoted the expression of both Arnt and AhR genes but only the Arnt gene showed statistically significant upregulation (FIG. 6(3)). Taken together, testing of various enzyme inhibitors to release AhR and Arnt genes from the epigenetically repressed state is achievable in A20 cells, which suggests (i) that arthritic B cells from mice might be reactive to these drugs and (ii) combined drug treatments is more effective.

Another embodiment as described herein, demonstrates epigenetic modifications that occur on histone proteins that either promote or silence transcription of neighboring genes. Similar to DNA methylation inhibitors, Ezh2 blockers were also developed primarily for cancer chemotherapy. EPZ6438 (Tazemetostat), one of the histone methyltransferase-specific drugs, is a first-in-class small molecule inhibitor of Ezh2 and is being tested in Phase II clinical trial programs for the treatment of various types of cancer. (Clinical Trial: *A Phase II, Multicenter Study of the EZH2 Inhibitor Tazemetostat in Adult Subjects With INI1-Negative Tumors or Relapsed/Refractory Synovial Sarcoma*). The potential of the methyltransferase inhibitor family in arthritis therapy and their evaluation in the context of RA will be investigated.

In another embodiment described herein, the effect of DNA methyltransferase inhibitors in mice with PG-induced arthritis is characterized. This characterization identifies gene targets of arthritis-specific epigenetic modifications through the investigation of genome-wide DNA methylation and accompanying gene expression changes in a progressive autoimmune murine model of RA. Primarily, the focus was on the analysis of the B cell methylome because epigenetic mechanisms are involved in B cell differentiation and antibody production. A number of epigenome modifiers were differentially expressed in arthritic B cells. By using the MIRA-chip method, several hundred promoters were found to be specifically methylated in arthritis (FIG. 1(A)), and gene expression studies detected several hundred genes that are also differentially expressed in arthritic B cells (FIG. 1(B)).

Relatively few, for example, about fourteen (14) genes were common on the lists of differentially methylated and differentially expressed genes, suggesting that most arthritis-related DNA methylation profile changes have no direct effect on gene regulation and can be considered as passenger epimutations.

In another embodiment described herein, the Ahr gene, which was hypermethylated in its promoter region in arthritic mouse B cells, and, accordingly, its expression was downregulated (FIGS. 1(C)-(E)). Ahr is a transcription factor that can bind both intrinsic and extrinsic ligands with high affinity, promoting its translocation into the nucleus where it regulates the expression of a plethora of genes. Regarding the nature of the regulation, gene activation is dominantly reported, but recent data prove that Ahr can also act as a transcriptional repressor, most likely due to its ubiquitin ligase activity. Stimulation of the Ahr gene impairs humoral immune response and suppresses B cell differentiation into immunoglobulin-secreting plasma cells.

Figure 1G:
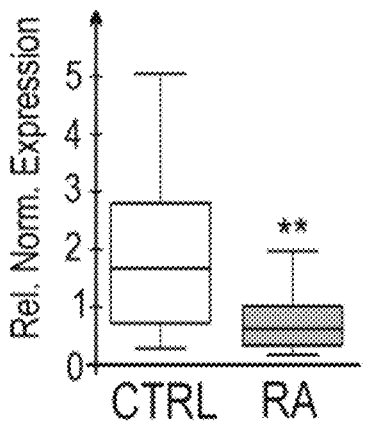
FIGS. 1(G)-(H) show differential gene expression and DNA methylation in human arthritic PBMCs.
Figure 1H:
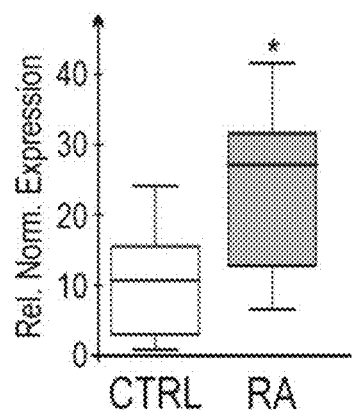
Figure 1I:
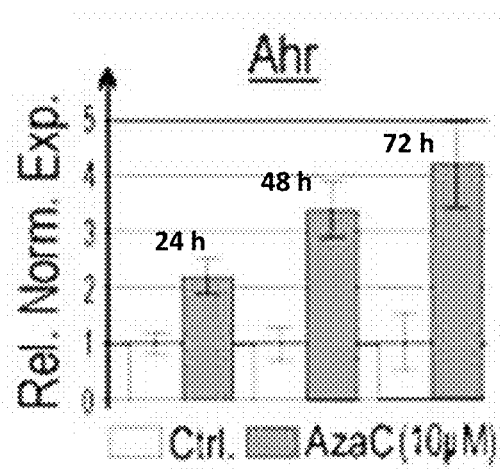
FIG. 1(I) illustrates AzaC-induced reactivation of Ahr expression in A20 cells after 24, 48 and 72 hours of drug treatment.

In a further embodiment, the critical role of Ahr in RA B cells was suggested by studies revealing downregulated gene expression in peripheral blood mononuclear cells (PBMC) of DMARD-naive (i.e., newly diagnosed patients who had not received DMARD treatment) RA patients (FIG. 1(G)).

In another embodiment described herein, the ability of DNA methylation inhibitor to restore Ahr expression in a B cell lymphoma line A20 (BALB/c origin), in which it was similarly inactivated by DNA methylation as in primary arthritic B cells was evaluated. A time course experiment with 10 µM of AzaC revealed that Ahr expression in A20 cells (FIG. 1(I)) could be reactivated. Employing AzaC at a higher concentration (20 µM), Ahr expression is restored even in ex vivo-cultured arthritic B cells (FIG. 1(J)). AzaC treatment not only increased Ahr mRNA expression but also resulted in the translocation of the translated product into A20 nuclei (FIG. 2(E)), suggesting that Ahr was ready for transcription factor activity.

Figure 2A:
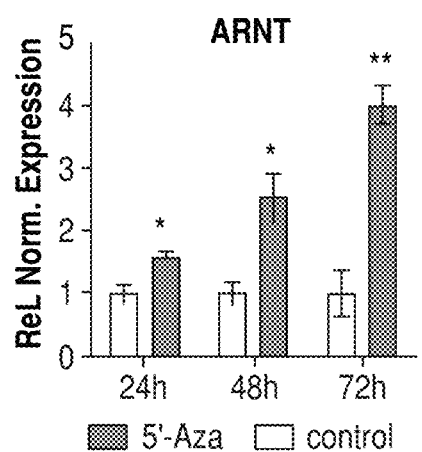
FIGS. 2A-2H illustrate that Ahr directly regulates Aicda expression in mouse B cells.
Figure 2B:
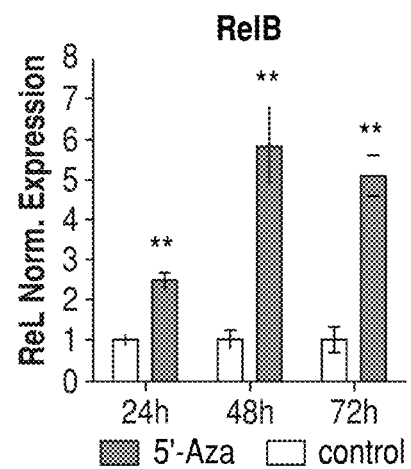

Ahr can interact with multiple transcription factors (TF) including Arnt and RelB as well as their cofactors, thus playing a role in transcription initiation or repression. Arnt and RelB were present in A20 cells, and the RelB expression was higher (FIGS. 2(A) and (B)) suggesting that canonical Arnt is not involved in the Ahr pathway, which can operate in B cells.

Investigations on the Contribution of Ahr to the Pathogenesis of Arthritis.

Ahr level is modest in follicular (Fo) and GC B cellsbut dominantly expressed in marginal zone (MZ) B cells which cells are also capable of forming GCs. Since Ahr is a bona-fide TF, its inactivation can induce a ripple effect and multiple genes could be affected. To explore Ahr-related gene regulatory cascades, potential Ahr-target genes were surveyed by comparing up- and downregulated gene sets of arthritic B cells with emblematic MZ- and GC-specific B cell genes (FIG. 2(C)). Aicda, which encodes Aid and catalyzes high-affinity immunoglobulin maturation, was one of the differentially expressed GC-specific genes in PGIA; implying that Aicda might be an Ahr target gene. It is noteworthy, both Ahr and Aicda genes were differentially expressed in B cells but their expressions were inversely correlated (FIG. 2(C)). Namely, Ahr expression was downregulated (i.e., due to DNA methylation-mediated silencing), while Aicda expression was one of the highest that could be measured in arthritic B cells. Thus, Aicda is supervised by Ahr, as supported by predicted Ahr binding sites in the regulatory regions of Aicda gene. To prove this hypothesis, the influence of Ahr on Aicda expression was investigated. In fact, extended exposure (i.e., 48 and 72 hours) of cells to AzaC similarly increased Ahr expression as we had observed before (FIG. 1(G)), and Aicda expression was significantly downregulated in A20 cells (FIG. 2(D)). AzaC-induced Aicda downregulation could be also observed at protein level in the cytoplasmic fraction of A20 cells (FIG. 2(E)). Thus, direct evidence was sought that the predicted Ahr binding site could be used as a landing site for Ahr, and it would trigger silencing of Aicda. Because the putative binding site of Ahr differs from the ChIP-Seq data defined Ahr consensus sequence (FIG. 2(F)), in vitro and in vivo DNA-protein interaction studies were introduced to assess its Ahr binding ability. Electrophoretic mobility shift assays (EMSA) with putative Ahr element harboring oligonucleotides indicated that Ahr can bind to the intronic element with high affinity and specificity (FIG. 2(G)). Chromatin immunoprecipitation studies with Ahr-specific antibody in A20 cells demonstrated that Ahr can also bind in vivo to the intronic element (FIG. 2(H)).

Results demonstrate that Ahr is the only TF that could be responsible for Aicda silencing, because (i) A20 cells and arthritic B cells are alike regarding Ahr and Aicda expression (i.e., Ahr is down, Aicda is up), (ii) AzaC treatment could revive Ahr expression, and (iii) by deploying shRNA-mediated gene silencing, Ahr could be downregulated with high specificity. The following experiment was conducted; A20 cells were transiently transformed with Ahr-specific shRNA-expressing constructs and treated with AzaC for 48 hours followed by RNA isolation and RT-qPCR. Control A20 cell cultures were treated with AzaC and transfected with plasmids not expressing Ahr-specific shRNA. Ahr expression was significantly increased in control cultures while the Aicda expression was downregulated (FIG. 2(I)).

However, in A20 cultures that received both AzaC and Ahr-specific shRNA treatments, Aicda was reversed indicating that Ahr was responsible for the silencing effect. The possibility that Aicda silencing can be attributed to any other AzaC reactivated TF (e.g. Azi229) was excluded. In fact, in vivo and in vitro data collectively approved the original hypothesis that Aicda is an Ahr-regulated gene and the dysfunction of Ahr-Aicda regulatory pathway may play decisive role(s) in arthritis pathogenesis.

Investigations on the Prophylactic Effect of AzaC on Arthritis Development in Mice with PGIA.

Figure 1J:
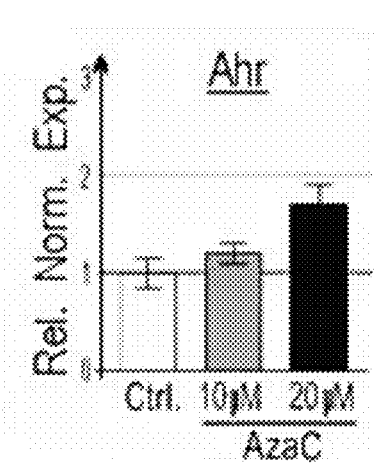
FIG. 1(J) AzaC-induced depicts reactivation of Ahr expression in ex vivo-cultured splenocytes. B cells were affinity purified before RNA isolation and subsequent RT-qPCR analysis.
Figure 1K:
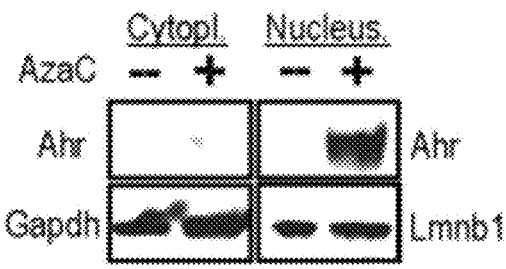
FIG. 1(K) is an image of Western Blot analysis of AzaC-treatment induced translocation of Ahr into nuclei. Ahr was investigated in subcellular fractions of A20 cells by Western blotting. Gapdh used for cytoplasm and Lamin 3 (Lmnb) for nucleus-specific loading controls. RT-qPCR experiments measured CT values were normalized to Actin-3 values. Ctrl: control. Values are the mean±SEM. ** p<0.01.
Figure 1L:
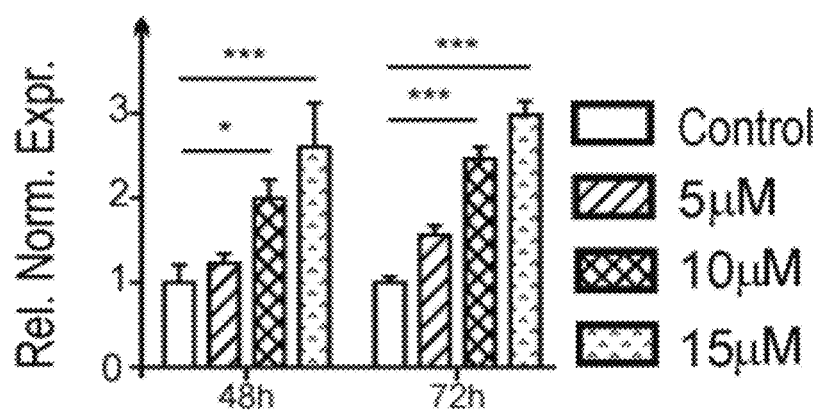
FIGS. 1(L)-(M) show Azacitidine (AzaC) induced gene expression changes in A20 cells.
Figure 1M:
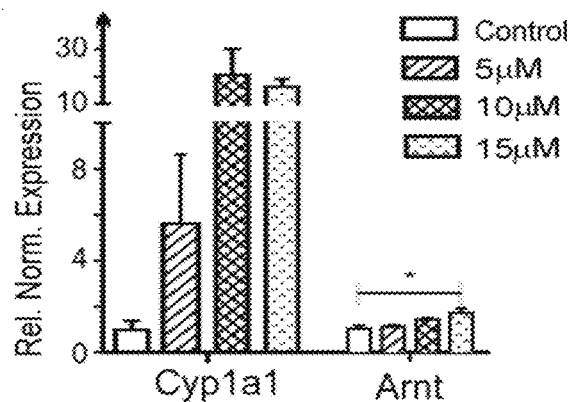
Figure 1N:
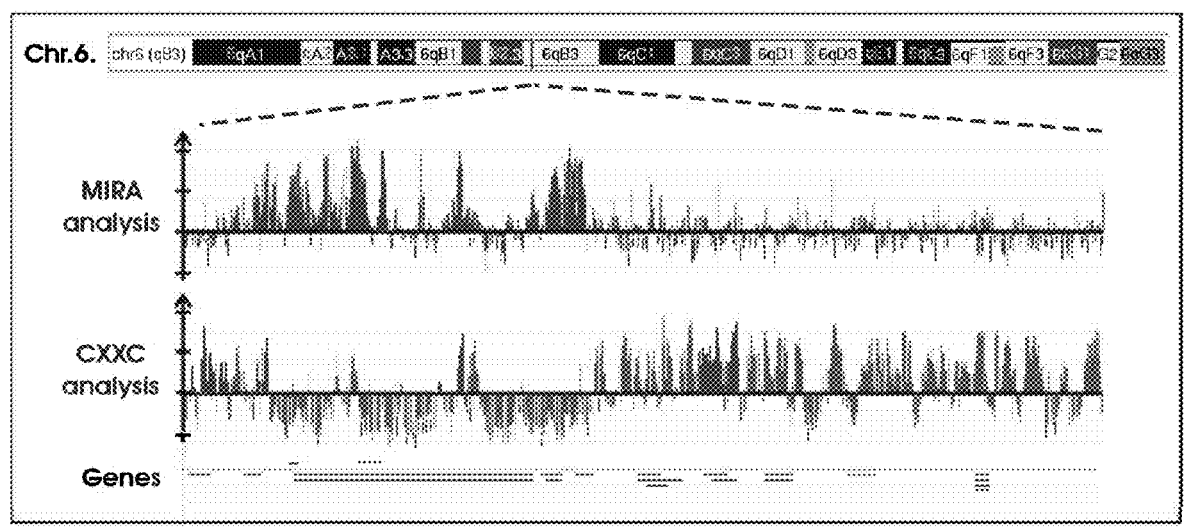

Because AzaC-treatment could reactivate Ahr expression both in B cell line A20 and in ex vivo cultured arthritic B cells (FIG. 1(J)), findings of the animal experiments were tested for the therapeutic potential of AzaC treatment. Based on the success with in vitro and ex vivo studies with AzaC, the therapeutic potential of AzaC on arthritic mice was tested. First, the prophylactic effect of AzaC on arthritis development in mice with PGIA was investigated. AzaC treatment was started 10 days before the expected PGIA onset (on day 40 of the immunization) and was administered intraperitoneally (i.p.) every other day. The control group received saline solution (FIG. 3(A)). AzaC treatment was shown to restore Ahr expression in vivo and prevent PGIA development or progression in mice (FIG. 3). Female BALB/c mice were immunized 3 times with PG. Limbs were inspected regularly after the third PG injection for signs of arthritis, and a visual arthritis score was assigned to all paws. No sign of the disease was observed neither around the expected onset time nor later during the course of the study (FIG. 3(A)). Only 10% (7.5 mg/m2) of the clinically applied dose of AzaC used for cancer therapy was administered. Visual arthritic score remained between 0 and 0.5 per animal indicating that low-dose AzaC treatment protected animals from PGIA (FIG. 3(A)).

Investigations on Beneficial Effect of AzaC Treatment on Established Polyarthritis.

In the therapeutic AzaC treatment group, arthritic mice were i.p. injected with either AzaC or vehicle on every other day following the first symptoms of arthritis, when the visual arthritis score was at least ≥2 per animal (FIG. 3(B)). AzaC-treatment proved to be very effective; two consecutive treatments could significantly reduce swelling and halt the progression of PGIA (FIG. 3(B)). AzaC treatment caused arthritis-associated DNA hypermethylation in the Ahr promoter region in arthritic mouse B cells (FIG. 3(C)), which was followed by increased expression of the Ahr gene. Restoration of Ahr in B cells induced the activation of a regulatory pathway, which likely led to the protection of the joints from inflammation. AzaC treatment reduced the DNA methylation level of the Ahr promoter as detected by MIRA (FIG. 3 (C)), which was accompanied by increased Ahr expression (FIG. 3(D)). There were no detectable histological differences between naive (non-immunized) and AzaC-treated "arthritic" ankles (FIGS. 3E and G). In contrast, untreated arthritis controls showed histological evidence of inflammation, synovial pannus formation, and cartilage and bone destruction in the investigated joints (FIG. 3(I)).

The Role of AzaC-Based Polyarthritis Therapy on Reconstruction of the Dysregulated Ahr-Aicda Regulatory Pathway.

Figure 3C:
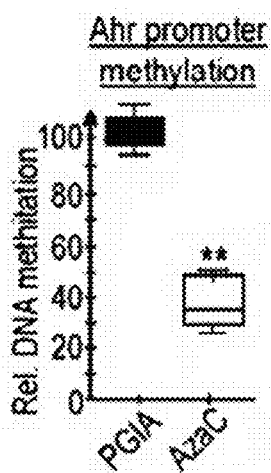
Figure 3D:
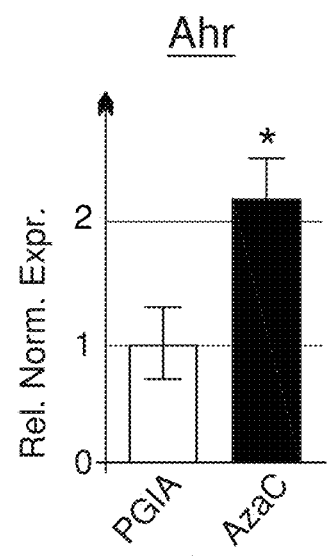
Figure 3E:
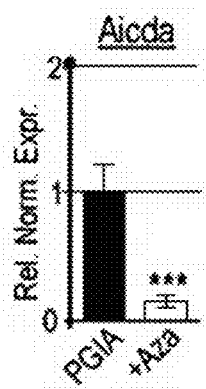
Figure 3F:
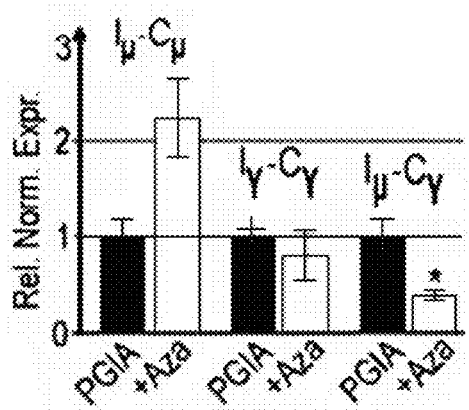
Figure 3G:
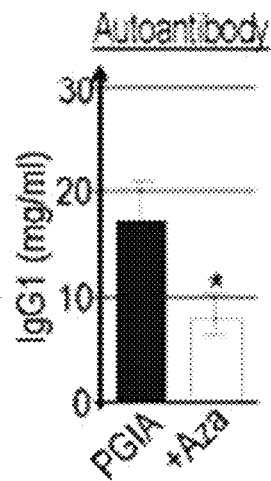
Figure 3H:
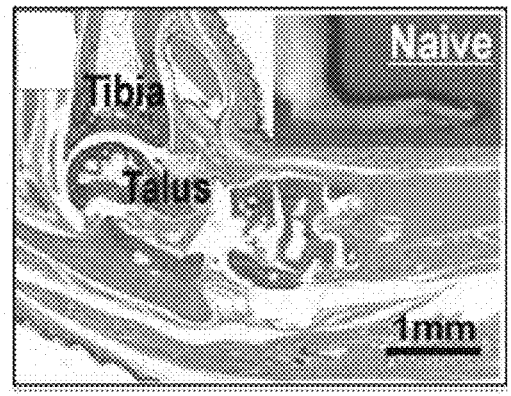
Figure 3I:
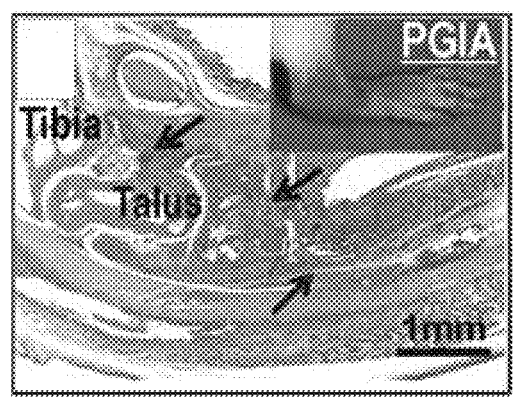
Figure 4A:
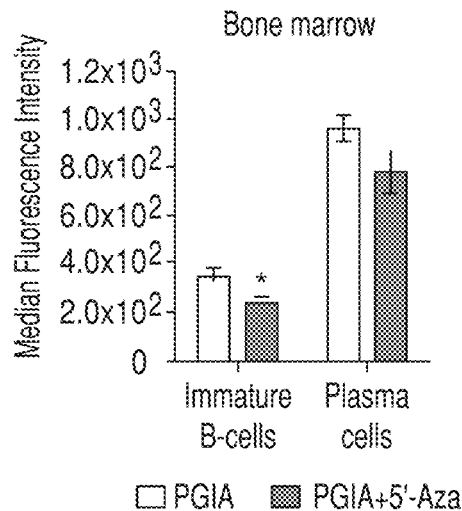
FIGS. 4A-D show that AzaC treatment induces impaired GC formation in secondary lymphoid organs.
Figure 4B:
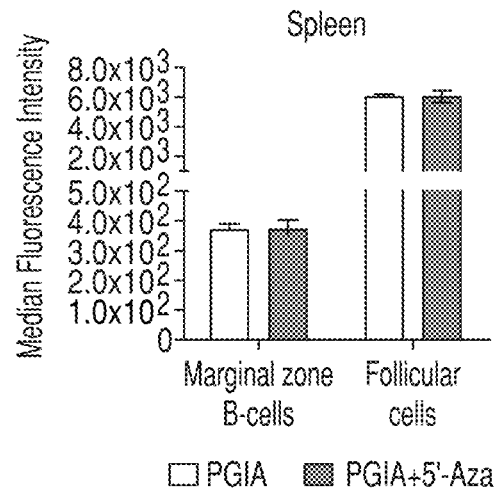
Figure 4C:
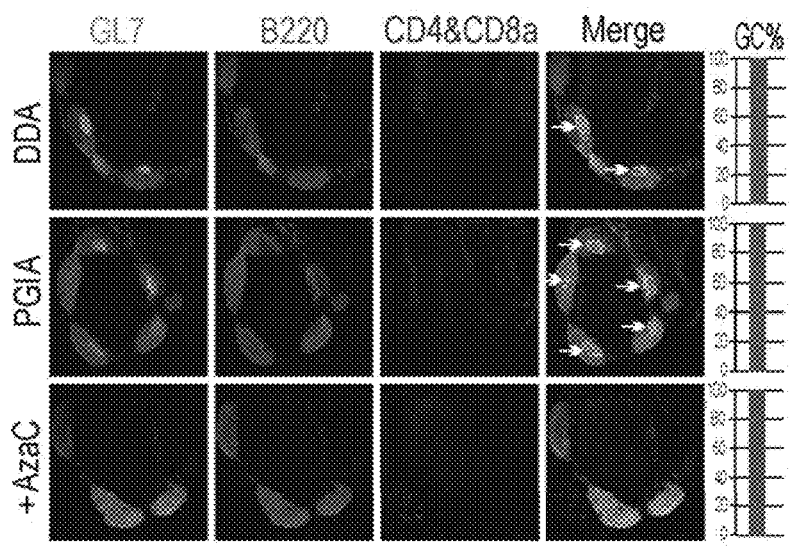
Figure 4D:
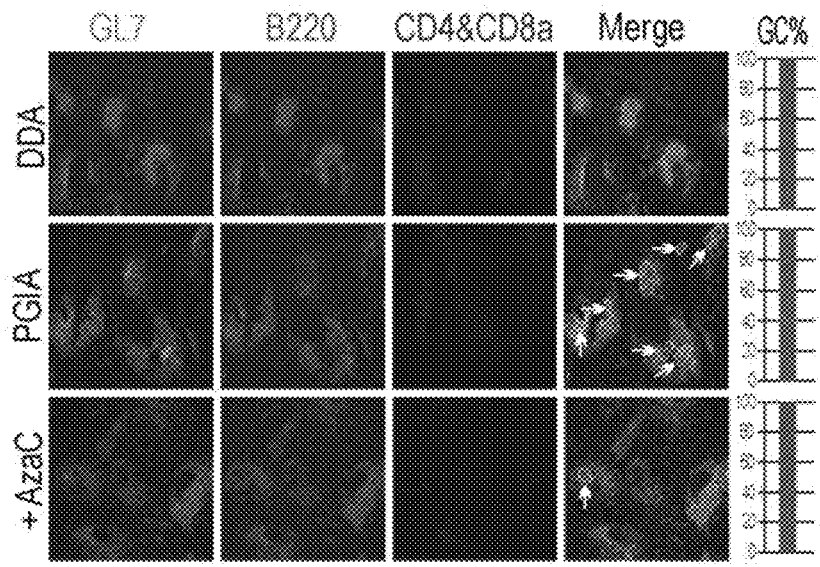
Figure 4E:
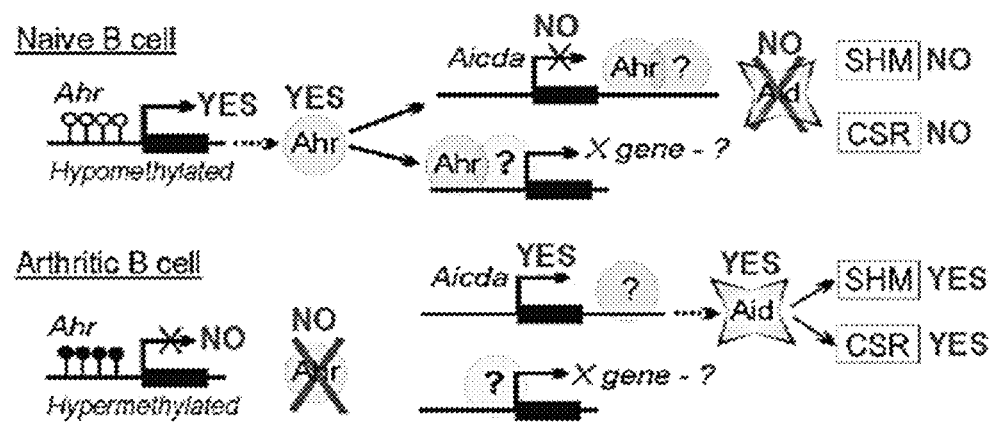
FIG. 4(E) is a schematic model of Ahr-Aicda regulatory pathway in naive and arthritic B cells.

Low-dose AzaC treatment proved to be sufficient for releasing Ahr expression from DNA methylation-mediated blockage (FIG. 3(C) (D)) and Aicda expression was markedly inhibited (FIG. 3(E)). Since Aicda is a key enzyme for class switch recombination (CSR), its high expression can account for the increased (auto)antibody production, measured in AzaC-treated arthritic animals (FIG. 3(G)). CSR was significantly affected by reduced Aicda expression inasmuch as post-recombinant IgG1 expression was decreased in AzaC-treated animals (FIG. 3(F)). AzaC-treatment had an impact on B cell development in bone marrow as flow cytometry detected significant decrease in immature B cell number and reduced, but statistically not significant alteration in plasma cell number (FIG. 4(A)). Regarding splenic marginal zone (MZ) and follicular B cell populations, no significant change could be observed in AzaC-treated animals (FIG. 4(B)). Since high-affinity antibody generation takes place in GCs, whether AzaC treatment affected GC formation was investigated. GC formation was monitored in control and arthritic mice, and in AzaC-treated animals (FIG. 4(C) (D)). AzaC treatment seriously impaired GC development and reduced GC number in both spleen and draining lymph nodes (FIG. 4(C) (D)). The Ahr-Aicda gene regulatory pathway is dysregulated in arthritic B cells (in mice and probably in humans as well), which significantly affect (auto)antibody formation and secretion (FIG. 4(E)). AzaC-treatment can restore Ahr expression and is sufficient to diminish autoantibody production and arthritis progression. These data provide an initiative for further studies to explore the therapeutic potential of low-dose DNA methyltransferase inhibitors in RA.

In another embodiment described herein, the lowest effective dose of a methylation inhibitor in the treatment and prevention of RA will be evaluated. AzaC triggers cytotoxicity and induces nausea, vomiting, fevers, diarrhea, rigors and many other side effects. The lowest AzaC dose that has an anti-arthritic effect was investigated. whether prolonged treatment could be maintained without serious side effects will be determined. Furthermore, the efficacy and cytotoxicity of DNA methylation inhibitors that possess different methods of action will be evaluated. In addition to AzaC and dAzaC, new drugs, which unlike AzaC and dAzaC, are not incorporated into the DNA will be proposed. One mode of action may be accomplished by binding to the active site of DNMTs or by allosterically blocking their activity.

In another embodiment described herein, (i) the lowest effective dose of AzaC by monitoring its action for an extended period of time, and (ii) and new alternatives to AzaC in arthritic mice will be determined.

In another aspect of the embodiment, AzaC treatment in arthritic mice will be characterized. AzaC proved to be a very effective anti-rheumatic drug at the employed dose (2 mg/kg) in mice, which was calculated on the basis of cancer-related mouse studies. Although arthritic mice tolerated the treatments surprisingly well, lower dose of AzaC could be sufficient for effective PG-induced arthritis management.

In a further embodiment, the following questions will be answered, whether (i) the employed dose can be reduced without losing significant protection against PG-induced arthritis, (ii) the two-week long AzaC regimen, which overlaps with the acute phase, can provide protection from the recurrence of the disease, and (iii) AzaC treatment for an extended period of time can induce serious side effects.

In another embodiment, the lowest effective dose of AzaC on established arthritis will be determined by setting up five (5) experimental groups of mice. The first group of arthritic mice will receive physiological saline (vehicle), and the second group will be treated with the same dose used in pilot studies. The next three (3) groups will be treated with 50%, 25%, and 10% of the original dose. The effectiveness of AzaC doses will be monitored for 1 month after the onset of the disease, which includes the 2-week-long acute phase and the first two weeks of the chronic phase of PGIA. A considerably lower AzaC dose would be sufficient for effective arthritis therapy. More specifically, in pilot experiments, the efficiency of AzaC treatment was highly significant ($p<0.001$); practically, there were no detectable signs of PGIA after the second AzaC injection. For further studies, an AzaC dose that is associated with a significance level of at least $p<0.01$ in the course of the one month experimental period will be selected.

Second, the ability of a previously defined minimal effective AzaC dose to prevent the recurrence of PGIA will be investigated. Arthritic mice will be distributed in three groups; the first one will be injected with saline (Control 1), while Group 2 and 3 will be treated with AzaC on every second day. After the end of the acute phase, Group 2 (control 2) will not receive more AzaC treatment but only vehicle. Treatment of Group 3 will be continued for three more months. The Control 1 group will help in defining the theoretical end of the acute phase, when AzaC treatment would be stopped in Group 2. A comparison of Group 2 to 3, will help with the investigation of whether any molecular and/or visual signs of PGIA appear after discontinuing AzaC treatment.

Finally, if the short-term AzaC treatment is found to be insufficient to prevent PGIA recurrence, then the potential ADEs associated with prolonged AzaC treatment will be investigated. Three experimental groups will be set up including Group 1—wherein no arthritis will be induced, Group 2—in which PGIA will be induced but not treated, and Group 3—wherein AzaC treatment will be started right after observing the first signs of arthritis and continued for 6 months. Defining ADEs in an animal model is not obvious; therefore, special attention will be paid to body weight changes and the appearance of the fur, eyes, posture and behavior. In addition, molecular signs of PGIA will also be inspected throughout the 6 months study period. It is expected that a low-dose AzaC regimen can keep PGIA at bay with mild side effects.

Epigenetic Characterization of AhR and Arnt Promoters in B Cells.

The most frequent gene silencing epigenetic signals are (i) DNA methylation at CpG dinucleotides, (ii) HDAC catalyzed deacetylation at histones H3 and H4, (iii) histone H3 tri-methylation at lysine 9 and (iv) tri-methylation of lysine 27 in histone H3. To reveal which type of epigenetic signal dominates in the silencing of AhR and Arnt, chromatin immunoprecipitations (ChIP-PCRS) with the appropriate antibodies (Table 2) will be conducted. B cells will be isolated using EasySep® mouse B cell Enrichment kits (StemCell Technologies) from arthritic and control BALB/c mice. A small aliquot ($\sim 10^5$ cells) will be retained to assess the purity of the enriched fraction by flow cytometry (FACSCanto, BD Biosciences). Purified cells (expected purity >95%) will be used for subsequent ChIP procedures. Separated lymphocytes will be divided into two parts; the smaller portion ($1-2 \times 10^6$) will be kept for simultaneous isolation of genomic DNA for DNA methylation profiling (i.e., MIRA analysis) and the larger portion ($6-7 \times 10^6$) will be used in ChIP-PCR experiments. Immediately after cell separation, cells designated for ChIP will be cross-linked with formaldehyde, and the chromatin will be fragmented into the appropriate size (~400 bp) by sonication. ChIP-PCR experiments with appropriate antibodies, listed in Table 2 will be conducted. It is worth noting that the absence of tri-methylation of lysine 4 in histone H3 is an indirect but decisive signal of gene inactivation, therefore, it will be investigated for control purpose.

TABLE 2

Antibodies for the proposed ChIP experiments

| ChIP-grade antibodies | Company | Cat.#: |
|---|---|---|
| Anti-Histone H3 (tri methyl K9) | Abcam | ab8898 |
| Anti-Histone H3 (di methyl K9) | Abcam | ab1220 |
| Anti-Histone H3 (tri methyl K27) | Abcam | ab6002 |
| Anti-Histone H3 (tri methyl K4) | Abcam | ab8580 |
| Rabbit anti-IgG (Control) | Abcam | ab46540 |

Multiple PCR primer pairs will be designed for the two promoter regions, and qPCR will be performed on the captured/reverse cross-linked/deproteinized DNA samples using a CFX Connect real-time PCR System (Bio-Rad, CA). To minimize the false detection rate, internal negative and positive controls for each sample will be employed, including Gapdh promoter (negative control, never silenced in any cell type) and Xist gene promoter (positive control, at least one copy of this non-coding RNA gene is always silenced). After conducting the proposed ChIP analyses, the types of epigenetic signals responsible for silencing the AhR and Arnt promoters will be determined and can thus help in employing the appropriate enzyme inhibitor(s) to subsequent experiments.

Testing Adequate Epigenetic Enzyme Blockers in B Cells.

In the light of the ChIP-PCR data, multiple drugs from appropriate enzyme inhibitor families will be chosen. At least two enzyme-specific blockers for each type of repressive signal in primary B cell cultures will be chosen. B cells from mice with PGIA and establish primary cell cultures will be isolated to determine the most effective drug for suspending transcriptional blockage. Cells will be treated for 72 hours using the drugs listed in Table 3 at different concentrations, based on data from the literature. At the end of the experiment, total RNA will be isolated from the cultures and the effect of the given drug on gene expression using qRT-PCR will be determined. The drugs that prove to be the most effective in the previous studies will be tested in ELISPOT experiments. Treatments will be checked for repression of autoantibody production of B cells. ELISPOT experiments can provide a very important layer of information regarding the beneficial effect of epigenetic enzyme inhibitors in arthritis treatment before animal studies.

transcription factors can directly or indirectly suppress autoantibody production of arthritic B cells and ultimately treat PGIA will be identified.

PGIA will be induced in mice, and after the onset of the disease, treatment will be immediately started with three different doses of the chosen enzyme inhibitor. Four different experimental groups will be established (control and 3 different dosage treatments) with 15 mice in each group. Pathological changes will be monitored by regular scoring (every second day) for 2-3 weeks. The first group of mice will be treated with doses proved to be optimal in published studies of cancer treatments (table 3). If there are no published data for the given enzyme inhibitor (e.g., BIX01294) then the starting dose that is published for its closest homolog will be used. The second group will receive half doses, and the third group will get one fourth of the original dose. At the end of the treatment, mice will be sacrificed, sera collected for measuring cytokines and autoantibodies, and total RNA and protein lysates will be extracted from affinity purified B cells (using antibody-coated magnetic beads) from the spleens. Once the lowest effective dose has been established for a 2-week treatment following the onset of PGIA, new treatment and control groups will be established, and the kinetics of the therapeutic effects will be monitored for up to 6 months. The focus of the investion will include the expression level of the AhR and Arnt genes using qRT-PCR and Western blots. Autoantibody levels will also be monitored by flow cytometry to compare and quantify the drug effects.

In another embodiment described herein, a combination of methylation inhibitors to be used in the treatment and prevention of RA will be determined, starting dose levels will also be determined. It is proposed that the starting dose for therapeutic treatment in a patient will be about 25% to about 50% of the dose used in cancer treatment. A combined application of DNA methyltransferases, histone methylation inhibitors, and epigenetic enzyme inhibitors will also be explored. It is possible that our results will reveal that combined treatment is more effective in suppressing antibody production by reviving the two transcription factors, AhR and Arnt. In this case, a combined application of the drugs in animal studies will be employed.

TABLE 3

Epigenetic enzyme inhibitors for reconstituting expression of AhR and Arnt genes

| Epigenetic Gene Silencing Signals(s) | Enzyme(s) | Inhibitor(s) | Employed Conc. Range Cell Culture | Mice |
|---|---|---|---|---|
| DNA Hypermethylation | | | | |
| | DNMTs | Azacitidine | 1-25 μM | 0.05-3 mg/kg |
| | DNMTs | RG108 | 1-50 μM | 0.05-6 mg/kg |
| Histone Methylation | | | | |
| Histone H3K27m3 | EZH2 | GSK126 | 10-100 μM | 10-100 mg/kg |
| | EZH2 | GSK126 | 1-50 μM | 10-100 mg/kg |
| Histone H3 K9m2 & m3 | G9a | BIX01294 | 10-100 μM | 10-100 mg/kg |
| | SUV39H1 | Chaetocin | 1-50 μM | 10-100 mg/kg |

Exploring the Therapeutic Effects of Epigenetic Enzyme Inhibitors in Mice with PGIA.

In an embodiment described herein, epigenetic enzyme inhibitor candidates that release transcriptional blockage of AhR and Arnt promoters, and revive the expression of these Evaluation of Alternative Hypomethylating Agents in Arthritic Mice.

Epigallocatechin-3-gallate (EGCG) and N-phthaloyl-l-tryptophan 1(RG108), are also DNA methylation-specific inhibitors that act by directly blocking DNMTs and display comparatively low cytoxicity. In vitro and ex vivo experiments were very informative regarding the hypomethylation-inducing potential of AzaC (FIGS. 1(G) and (I)) and this approach is helpful in selecting the most promising drugs for animal studies. First, the ability of EGCG and RG108 to erase DNA hypermethylation of the Ahr promoter and revive Ahr expression in A20 cells and ex vivo cultured arthritic B cells will be investigated. Additional DNA methylation inhibitors will also be investigated. These alternative drugs include SGI-1027 and Lomeguatrib. In case of an effective reactivation of Ahr expression in primary arthritic B cells, the studies will be continued in in vivo animal studies.

Drug treatments will be started in animals with established arthritis at four (4) different doses. Five (5) experimental groups will be set up (1 control and 4 drug-treated groups). Group 1 (control) mice will be treated with the appropriate vehicle of the drug. Group 2 mice will be treated with doses that have provided optimal results in published animal studies. The other three groups will receive 50%, 25% and 10% of the original, starting dose for a month-long experimental period. Serum and organ samples will be collected for molecular and histopathological studies to evaluate the therapeutic potential of the AzaC alternatives as anti-arthritic agents.

Figure 3J:
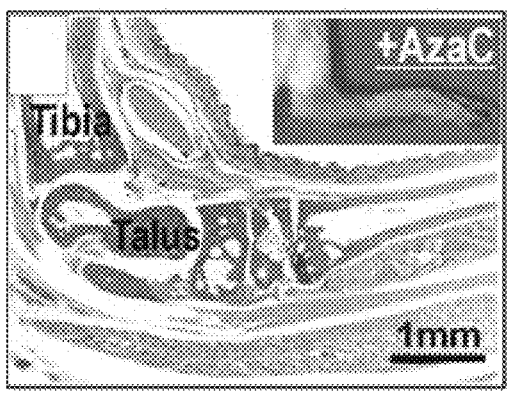

It is expected that at least one of the evaluated DNA methylation inhibitors will be similarly effective as AzaC in the pilot studies (FIG. 3(J)). The unprecedented development of epigenetics including drug design, which is frequently guided by 3D molecular structure information, aids a prediction that new hypomethylating drugs will emerge in the near future. If the upcoming 3 years yield a novel effective DNA methylation inhibitor with low toxicity, we will then incorporate it into the studies and evaluate its anti-arthritic potential in PGIA.

Exploration of the Therapeutic Potential of Histone Methyltransferase Inhibitors.

Another embodiment directed to the exploration of the therapeutic potential of histone methyltransferase inhibitors described here is organized into two parts; the first part addresses how Ezh2-mediated histone methylation cooperates with DNA methylation and generates an arthritis-prone milieu in B cells. The second part will clarify the therapeutic potential of histone methyltransferase inhibitors and will also investigate whether combined use of DNA- and histone-methylation blockers might have an advantage over their separate application.

Figure 2C:
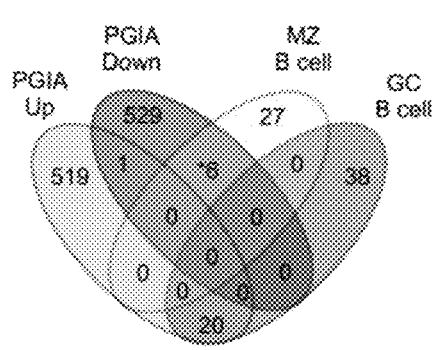
Figure 2D:
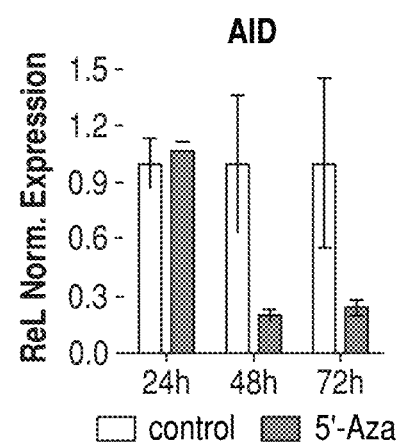
Figure 2E:
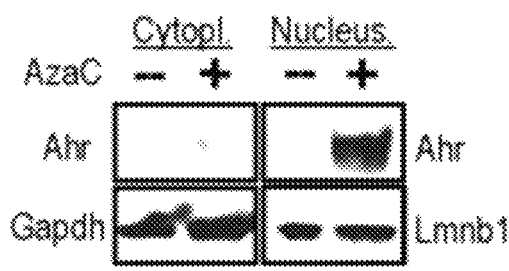
Figure 2F:
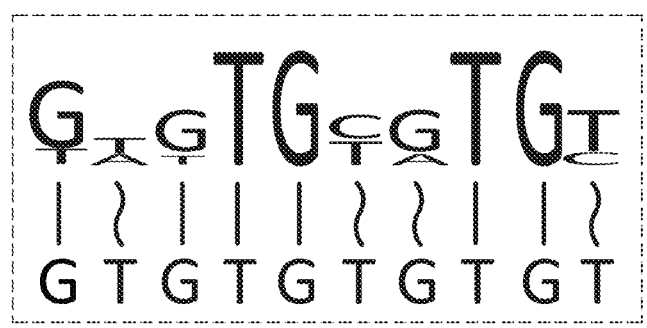
Figure 2G:
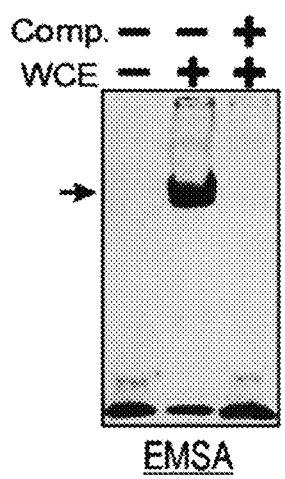
Figure 2H:
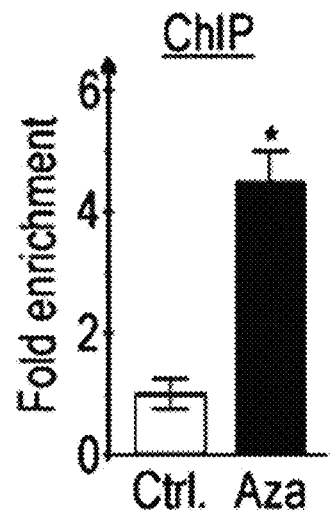
Figure 2I:
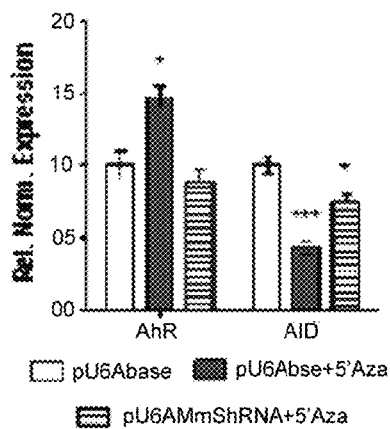
FIG. 2(I) demonstrates that Ahr is exclusively responsible of Aicda downregulation after AzaC-treatment. A20 cells were electroporated with Ahr-specific shRNA expressing construct or control (shRNA not expressing) plasmid followed by AzaC treatment, gene expression was monitored by qRT-PCR. Values are the mean±SEM. * p<0.05, ** p<0.01.
Figure 2J:
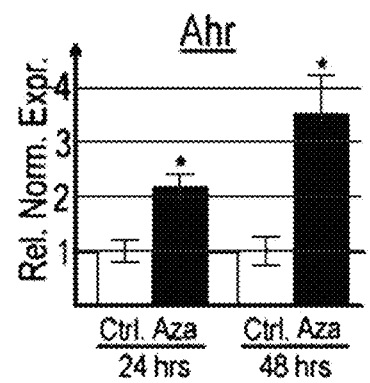
FIG. 2(J) describes Ahr expression at 24 hours and 48 hours after AzaC-treatment.

In an aspect of the embodiment described herein, an Ahr-related regulatory pathway was explored and potential Ahr-target genes were identified by comparing up-regulated and downregulated gene sets in arthritic B cells with characteristic marginal zone-(MZ) and germinal center (GC)-specific B cell genes (FIG. 2(C)). It was found that mostly GC-specific genes (n=20 in FIG. 2(C) were differentially expressed in arthritic samples, indicating that antibody production could be dysregulated. Activation-induced cytidine deaminase (Aicda), one of the genes showing the highest expression, encodes an enzyme that is involved in high-affinity immunoglobulin maturation by catalyzing certain steps of somatic hypermutation (SHM) and class switch recombination (CSR). In addition, a very recent study demonstrated that Aicda is also implicated in remodeling of the methylome in GC B cells, which proved to be significantly conserved between mouse and human B cells. Microarray data (FIG. 1(A-B)) revealed that both the Ahr and Aicda genes were differentially expressed in B cells, but their expression levels were inversely correlated (FIG. 2(C)). Namely, Ahr expression was downregulated due to DNA methylation-mediated silencing, while Aicda expression was one of the highest that could be measured in arthritic B cells. This demonstrates that Aicda is a member of the Ahr-supervised regulatory network that transmits Ahr action onto effector genes. Ahr directly regulates Aicda by binding to its intronic region (FIGS. 2(G-H)). With extended exposure of A20 cells to AzaC (i.e., 24 and 48 hours), Ahr expression significantly increased (FIG. 1(D)), and Aicda expression was significantly downregulated (FIG. 2(K)).

In another embodiment described herein, Ahr directly regulates Aicda expression in mouse B cells (FIG. 2(K-L)). ChIP demonstrates that Ahr can bind to the intronic region of the Aicda gene in vivo (FIG. 2(H)). AzaC treatment releases Ahr from DNA methylation-mediated silencing in A20 cells (FIG. 2(J)). AzaC treatment reduces Aicda expression in A20 B cells (FIG. 4(E)). Ahr is exclusively responsible for Aicda downregulation after AzaC treatment. A20 cells were electroporated with an Ahr-specific shRNA-expressing construct or control (shRNA not expressing) plasmid followed by AzaC treatment; gene expression was monitored by qRT-PCR. Mean±SEM. (*p<0.05, **p<0.01) (FIG. 2(L)).

To confirm that AzaC-induced suppression of Aicda was mediated by the reactivated Ahr, Ahr expression was knocked down using Ahr-specific shRNA. Observations show that, (i) Ahr and Aicda expression are similar in A20 cells and arthritic B cells (i.e., when Ahr is down, Aicda is up), (ii) AzaC treatment could restore Ahr expression and (iii) by deploying shRNA-mediated gene silencing, Ahr could be downregulated in a highly specific manner. Accordingly, following experiment was conducted; A20 cells were transiently transformed with Ahr-specific shRNA-expressing constructs and treated with AzaC for 48 hours followed by RNA isolation and qRT-PCR. Control A20 cell cultures were treated with AzaC and transfected with plasmids not expressing Ahr-specific shRNA. Ahr expression was significantly increased in control cultures, while the Aicda expression was downregulated (FIG. 2(L)). However, in A20 cultures that received both AzaC and Ahr-specific shRNA treatments, Aicda expression was reversed, indicating that Ahr was responsible for the silencing effect. These data demonstrate that Ahr acts as a negative regulator of Aicda and likely contributes to the suppression of antibody maturation.

In another embodiment, disease-suppressing AzaC therapy (FIG. 3(A-(B)) by restoring the dysregulated Ahr-Aicda-Antibody maturation pathway is demonstrated. AzaC treatment proved to be sufficient for rescuing Ahr expression from DNA methylation-mediated blockage (FIG. 3(C-D), and Aicda expression was markedly inhibited in arthritic mice (FIG. 3(E)). AzaC treatment reactivated Ahr expression in mice with PGIA (FIG. 3). AzaC treatment reduced the DNA methylation level of the Ahr promoter detected by MIRA (FIG. 3(C)), which was accompanied by increased Ahr expression (FIG. 3(D) and suppressed Aicda expression as monitored by qRT-PCR (FIG. 3(E). Downregulated Aicda expression induced impaired CSR. Human PG-specific IgG1 concentration was determined by ELISA in sera of control mice (i.e., untreated PGIA) and AzaC-treated PGIA mice (FIG. 3(F)).

Since Aicda is a key enzyme for Class Switch Recombination (CSR), its high expression accounts for the increased class-switched (auto)antibody production in arthritic animals. Germline transcripts (Ip-Cμ and Iγ1-Cγ1) and post-recombination transcripts (Ip-Cγ1) of the IgG locus were quantified by qRT-PCR in splenic B cells of control with PGIA and AzaC-treated mice with PGIA (FIG. 3(G)). In AzaC-treated animals, CSR was compromised, which was reflected by the significantly decreased level of post-recombinant IgG1 mRNA species (Iμ-Cγ) compared to that of germline-specific transcripts (Iμ-Cμ and Iγ-Cγ) (FIG. 3(F)). Accordingly, the autoantibody titer was also found significantly reduced in sera of AzaC-treated PGIA mice (FIG. 3(G)).

In another embodiment, the effect of AzaC treatment on germinal center (GC) formation in animals was investigated. Germinal center formation was examined in control (DDA adjuvant-injected and arthritic non-treated) and arthritic AzaC-treated mice (FIG. 4(C-D)). It was observed that AzaC treatment seriously impaired GC development in secondary lymphoid organs and reduced their number in both draining lymph nodes and spleen FIG. 4(C-D)). Joint-draining lymph nodes (FIG. 4(C)) and spleens (FIG. 4(D)). DDA-injected (adjuvant control), vehicle-treated mice with PGIA and AzaC-treated mice with PGIA. Green-GL7 (activated B and T cell marker), Red-CD45/B220 (B cells), Blue-CD4 & CD8a (T cells). Arrows point to GCs. GC %-percentage of GC-containing follicles observed in the investigated lymph nodes and spleens (n=36 follicles from LNs, n=106 follicles from spleens). Green sidebars-percentage of GC carrying follicles. Red sidebars are follicles without GC.

In another aspect of the embodiment, a gene regulatory network in B cells that supervises GC formation and high affinity class-switched antibody production was investigated. This "Ahr→Aicda→GC formation→antibody production" cascade is inactivated by silencing of the Ahr promoter via DNA hypermethylation in arthritic B cells. These data suggest that DNA methylation-mediated gene silencing is a causative factor in arthritis. Effective gene inactivation can be achieved via a complex multistep process wherein DNA methylation is just one of the involved mechanisms. It is hypothesized that there could be additional druggable enzymes for gene silencing, and their targeted inhibition might have the same or even better effect than blocking DNA methylation. In fact, there is a mechanism that also generates transcriptional repression and gene silencing by tri-methylation of lysine 27 in histone H3. Indeed, the Ezh2 enzyme-mediated histone tri-methylation precedes DNA methylation and can be considered a forerunner that generates the appropriate milieu for DNA methylation. DNA methylation and Ezh2-mediated histone methylation are linked, and indeed, auxiliary proteins that play a role in defining the subsequently silenced genes have been discovered. Importantly, one of these auxiliary proteins is encoded by the Phf19 gene, which was revealed to be a highly significant arthritis risk gene found in a GWAS conducted on 100,000 individuals (29,880 RA cases and 73,758 controls).

Mechanistically, Phf19 facilitates recruitment of an Ezh2-containing tri-methylation complex to previously active genes eventually leading to gene silencing. Thus, Phf19 defines which set of genes will be ultimately inactivated by DNA methylation. In addition, B cell-focused microarray studies (FIG. 1(B)) found that the Phf19 and Ezh2 genes were specifically upregulated in arthritis, and these findings were confirmed by qRT-PCR experiments (FIGS. 7(A-B)).

Gene Expression Studies of Mouse and Human Phf19 and Ezh2.

Figure 7A:
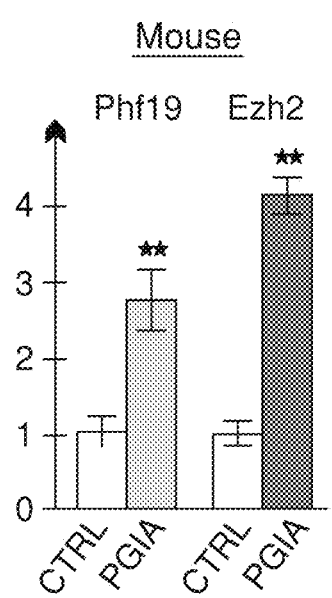
FIGS. 7A-B are charts showing results of gene expression studies of mouse and human Phf19 and Ezh2.
Figure 7B:
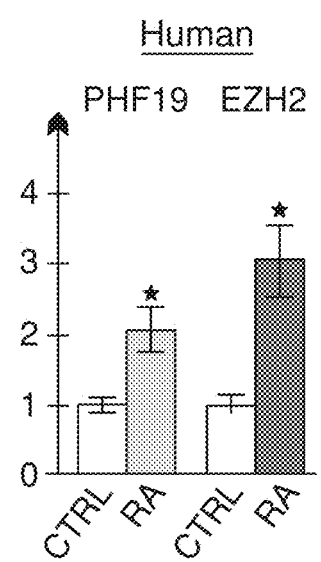

In another embodiment, the function of Phf19 and Ezh2 genes in arthritis pathogenesis is shown, using Phf19/Ezh2 gene expression data in mouse B cells from the spleens of adjuvant-injected controls (CTRL, white columns) and arthritic mice (PGIA, gray columns) (n=4) (FIG. 7(A)). PHF19/EZH2 gene expression in human peripheral blood mononuclear cells (PBMCs) is also evaluated. The white bars represent healthy controls (CTRL, with baseline [1-fold] expression), and the gray bars show relative expression changes measured using qRT-PCR in the PBMCs obtained from healthy individuals (n=5) and treatment-naive RA patients (n=16) (*$p<0.05$, **$p<0.01$) (FIG. 7(B)). Upregulated expression of these two genes in DMARD-naive RA patients (FIG. 7) was detected, providing additional strong evidence that Phf19 and Ezh2 are indeed involved in the pathogenesis of arthritis.

In another embodiment described herein, the function of the Phf19/Ezh2 genes in arthritis pathogenesis is determined. Knock-out (KO) mice were generated in which both Phf19 alleles were deleted and replaced with a targeting vector carrying the LacZ-Neo cassette. (FIG. 8). Ablation of the Phf19 gene from the mouse genome did not change viability, and no obvious phenotypic or physiological alterations were observed. Phf19-deficiency in the BALB/c genetic background is required to assess PGIA susceptibility. To this end, the original founder knock-out (KO) mice was back-crossed and their offspring with BALB/c mice in 10 generations. Currently, the first breeding pairs of homozygous animals carrying Phf19-null alleles in the BALB/c background have been created, but their arthritis susceptibility has not been tested yet. These homozygous animals are being bred to generate a sufficient number of Phf19−/− KO mice for the proposed experiments. PCR genotyping show that the wild type mice carry the original Phf19 gene, while KO1 and KO2 mice have no Phf19 alleles (FIG. 8(B)).

DNA methylation and Ezh2-mediated histone methylation act in concert to achieve effective gene-specific silencing. Pilot experiments revealed that Phf19 and Ezh2 genes are specifically upregulated in B cells of arthritic mice. A new druggable enzyme (Ezh2, histone methyltransferase) is incorporated into the RA murine model (FIG. 9). Red arrow points to a GWAS-identified RA risk gene. Green arrows indicate druggable genes. Dnmts—DNA methyltransferases. (FIG. 9).

In another embodiment, a unique experimental tool for clarifying the function of Phf19/Ezh2 in B cell maturation and arthritis is described. Homozygous Phf19-deficient mice in the BALB/c background provide a unique experimental tool for evaluating the function of Phf19/Ezh2 in B cell maturation and arthritis. Although dysregulated expression of Phf19 may be the ultimate reason for arthritis-specific histone methylation and DNA methylation, the druggable component of this system is the Ezh2 enzyme. Ezh2 blockers have never been studied in experimental arthritis, evaluation of the therapeutic potential of Ezh2-specific inhibitors (e.g., CPI-120564 and Tazemetostat) in the RA murine model is proposed. Combined applications of drugs in RA therapy may allow for lower doses of the individual drugs to achieve the same therapeutic effect as high doses of individual agents.

Investigation of the Contribution of Phf19/Ezh2 Genes to Arthritis in Mouse B Cells.

In an embodiment described herein, Phf19 KO BALB/c mice will be used to unravel how Phf19/Ezh2-mediated histone methylation and DNA methylation control silencing of anti-inflammatory genes. The anti-inflammatory genes are not necessarily direct targets; therefore, an indirect approach, including DNA and histone methylation and gene expression analyses, must be employed.

First, KO mice will be evaluated to determine whether animals with the null allele (Phf19−/−) show resistance or reduced susceptibility to PGIA. It is expected that deletion of the Phf19 gene will decrease arthritis susceptibility in KO animals compared to that in the wild-type mice. To test this hypothesis, PGIA will be induced in control (wild-type littermate BALB/c) and Phf19−/− mice, and pathological changes will be monitored. In pilot experiments, it was observed that PGIA is associated with extensive germinal center (GC) formation in secondary lymphoid organs (FIGS. 4(C-D)), which was diminished after AzaC-mediated reactivation of Ahr. Therefore, organ samples will also be collected (spleen, lymph nodes and paws) for microscopic analysis of GC formation and joint histopathology in wild-type and Knock-out (KO) animals.

Next, the Phf19 ablation-provoked molecular changes will be investigated, including DNA and histone methylation in B cells. Purified B cells will be divided into three groups; Group 1 (~2×10$^6$ cells) will be used for DNA and total RNA isolation, while chromatin immunoprecipitation (ChIP) will be conducted in cells (6-7×10$^6$ cells) from Group 2 and 3 using anti-Ezh2 and anti-Phf19 ChIP-grade antibodies. Nucleic acid purification will be conducted using a special kit (ZR-Duet™ DNA/RNA MiniPrep, Zymo Research, CA), which allows for simultaneous purification of genomic DNA and total RNA from the same cells. In proof-of-concept experiments, MIRA-chip and gene expression microarrays were used to identify arthritis-related genes (FIGS. 1(A-B). New technologies (i.e., MIRA-Seq and RNA-Seq) provide even better coverage of the methylome and have an increased chance of identifying new regulatory regions and alternative transcripts. Accordingly, the B cell-specific DNA methylation profiles will be explored using the MIRA-Seq method, while the accompanying gene expression will be determined by RNA-Seq. Immediately after B cell separation, cells designated for ChIP will be cross-linked with formaldehyde, and the chromatin will be fragmented into the appropriate size (~400 bp) by sonication. For ChIP, an optimized protocol for mononuclear cell analysis (ChIP-IT® PBMC kit, Active Motif, CA) will be used. Next-generation sequencing (NGS) data on a selected set of genes employing individual ChIP-PCR, bisulfite sequencing, and qRT-PCR methods will be verified. The rationale of gene selection is that ablation of Phf19 releases the targeted genes from the silenced state, allowing them to be highly expressed in B cells of KO mice. These genes will be considered bona fide targets of Phf19/Ezh2, and their epigenetic inactivation may have arthritis-promoting potential. It is expected that a number of genes that are known for being involved in inflammatory processes will be among the bona fide Phf19/Ezh2 target genes. More specifically, it is expected that anti-inflammatory genes will dominate among the targeted genes, which would explain the hypothesized arthritis resistance of Phf19−/− KO mice.

Investigating the Therapeutic Effects of Targeted Inhibition of Ezh2-Mediated Histone Methylation in Arthritic Mice.

In another embodiment, therapeutic effects of targeted inhibition of Ezh2-mediated histone methylation in arthritic mice is described. Pilot experiments demonstrate that DNA methylation-specific inhibitor AzaC treatment prevents the development of arthritis and halted the progression of PGIA. Molecular studies revealed that DNA methylation is mechanistically preceded by Ezh2-mediated histone methylation, which is a key event in gene silencing. It is hypothesized that selective inhibition of histone methylation would block subsequent DNA methylation and might also interfere with arthritis development (FIG. 9). Ezh2-specific inhibitors are commercially available, and PGIA is an excellent model for testing their therapeutic potential.

As histone methyltransferase inhibitors have never been investigated in the context of arthritis, the anti-arthritic effect of three Ezh2 blockers EPZ005687, GSK343 and GSK503 will be evaluted. The proposed agents have a high affinity to Ezh2 (Ki values are in the low nM range) and >1000-fold selectivity against other histone methyltransferases. In various cancer models, the listed drugs have already been tested and have shown therapeutic potential. The anti-arthritic potential in five (5) experimental groups of PGIA mice will be investigated, including a vehicle-receiving control group and four (4) drug-treated groups. Published studies will be relied on for selecting the doses to be employed. The first group will be treated with the dose that was proven to be effective in the published studies, and the other three groups will receive 50%, 25% and 10% of the original dose. Treatment of mice will begin after the first signs of PGIA and continued for four (4) weeks. Inflammation-associated cytokine and autoantibody levels will be determined from the serum samples collected at the end of study. Treatment-induced epigenetic and gene expression changes will also be investigated. It is expected that blocking histone methylation will also compromise DNA methylation, thereby reducing arthritis severity or at least delaying the onset of arthritis compared to the vehicle-treated control animals with PGIA.

Use of Multiple Drugs to Maintain Low Disease Activity, and Prevent the Progression of Arthritis into a More Advanced Stage is a Fairly Standard Approach in the Treatment of Complex (Systemic) Diseases Such as RA.

In an embodiment described herein, the ability of combined application of DNA and histone methyltransferase blockers to lower the previously determined effective doses and still maintain their anti-arthritic effect will be investigated. The rationale behind this experimental strategy is that these inhibitors affect different enzymes but the same gene silencing mechanism (FIG. 9), thus concomitant inhibition might be more effective in normalizing or restoring B cell-specific gene expression patterns. To study this concept, two inhibitors that are the most effective in the targeted DNA methylation or histone methylation studies will be chosen. The chosen inhibitors will be i.p. administered into mice in three (3) doses. First, the effect of the optimal concentration of the two drugs previously found on PGIA will be assessed. Next, animals with PGIA will be treated with smaller (e.g., 50% and 10%) doses. The combined drug effects only on established PGIA using the experimental strategies and analyses described in the previous sections will be assessed.

In an aspect of the embodiment, animal model and proposed methods for drug evaluation will be described. For the drug-related studies, the PGIA model will be used, which can be induced in BALB/c mice by three immunizations (separated by three weeks) with purified human cartilage proteoglycan (PG) aggrecan. The onset of PGIA is very predictable; the first signs of arthritis (redness and swelling of the paws—acute phase) can be observed 9-10 days after the third immunization. Seven days after the onset of arthritis, the redness and swelling of the paws gradually declines; meanwhile, articular joints are destroyed and ankylosed (chronic phase). PGIA is an excellent mouse model of seropositive progressive polyarthritis such as RA.

To examine the effectiveness of drug treatments, the observation that PGIA is the only arthritis model in which most diagnostic biomarkers of RA are simultaneously present (RF, ACPA and anti-PG antibodies) will be exploited, all of which can be monitored from a few drops of blood collected either from the retro-orbital venous plexus or facial vein. The proposed experiments will be started after noticing the onset of PGIA, and the selected drug(s) will be i.p. administered on every other weekday. There will be fifteen (15) mice in each experimental group, and studies will be continued for (four) 4 weeks or six (6) months in case of the long-term (ADE-focused) studies. The severity of arthritis will be inspected three (3) times a week and visual arthritis scores will be assigned to each limb. Since there is no information regarding the effectiveness of these epigenetic enzyme blockers in the context of arthritis, we will also measure the diameter of joints with calipers to be able to detect the slightest changes. At the end of the experiments, whole blood will be collected, and the ELISA method will be used to measure autoantibody and inflammatory cytokine levels in sera. B cells will be affinity purified (i.e., immunomagnetic purification) from spleens for molecular analysis of DNA and histone methylation profiles using MIRA-Seq and ChIP-seq methods. Gene expression will also be explored using the RNA-Seq method, which can reveal how the drug-induced epigenetic changes alter gene expression. In addition to the molecular characterization of the triggered epigenetic and gene expression changes, the association of macromolecular events with drug treatment outcomes will be investigated. More specifically, the ability of these treatments to suppress inflammation and protect cartilage and bone in joints will be studied. For this purpose, limbs will be collected from the treated and control animals for histopathology evaluation. Pilot studies reveal that targeted blocking of DNA methylation results in compromised GC formation; therefore, the structure of joint-draining lymph nodes will also be investigated using immunohistochemistry.

Epigenetic and Gene Expression Profile Mapping in RA Patients.

In an embodiment described herein, similarly hypermethylated genes in mice and human arthritic B cells will be identified, and if the methylation status of these genes is reversible in PGIA by any of the investigated drugs, then it can be inferred that the given drug will also be effective in RA.

Similarly up- and downregulated genes in arthritic mouse and RA samples have been identified, which imply that PGIA recapitulates the epigenetic aspects of RA and provides valuable hints related to human studies. In preliminary studies, a search was conducted for epigenetic factors that play a role in long-term silencing or activation of genes (i.e., Polycomb and Trithorax family genes). Arthritis-associated expression of these factors in B cells isolated from arthritic mice or RA patients and found that four (4) genes were similarly upregulated and one was similarly downregulated (FIG. 10) was studied. Early observation that Phf19 and Ezh2 genes are upregulated in arthritis (FIG. 7) was confirmed by these studies. In addition, upregulated arthritis-specific expression of DNA methyltransferase 1 (Dnmt1) and Cbx5 genes was also detected. The only consistently downregulated gene was Ring1, which is also involved in certain gene silencing mechanisms. These PCR array-based findings confirm that the regulatory mechanisms implicated in mouse and human B cells are similar in the context of arthritis and suggest that similar therapeutic targeting strategies can be successful in PGIA and RA.

Arthritis-associated changes in the expression of epigenetic factors in arthritic mouse and human B cells are shown in FIG. 10. PCR-array heatmaps of gene expression changes in mouse (FIG. 10(A)) and human B cells (FIG. 10(B)). Red squares indicate upregulated genes; green squares indicate downregulated genes. RNA samples from arthritic B cells (PGIA or RA) were compared to that from control (adjuvant-treated or healthy human subject). Similarly upregulated genes are B04 (Cbx5), B11 (Dnmt1), C06 (Ezh2) and E08 (Phf19); the downregulated gene is F03 (Ring1). The differentially expressed genes shared between PGIA and RA are circled.

The previously employed PCR array platforms allowed an investigation of only a limited number of genes. It is plausible that by employing more advanced technologies such as RNA-Seq and MIRA-Seq, a number of differentially methylated regions and altered genes can be identified. DNA methylation and gene expression profile changes in B cells isolated from Ficoll-separated PBMCs of control human subjects and RA patients will be explored. The focus will be on those differentially methylated and expressed genes that can be linked to altered expression of neighboring genes, which implies that targeted drug treatment might have a significant therapeutic effect. Ezh2-mediated histone methylation changes will not be investigated at the genome-wide level (i.e., ChIP-Seq) in this specific aim because the potentially available cell number could be a limiting factor. However Ezh2-related histone methylation will be examined in a selected set of genes if warranted by the DNA methylation and gene expression data.

Identification of Genomic Regions in B Cells that Undergo Similar Epigenetic Alterations During PGIA and RA.

In an embodiment described herein, it is shown that B-lymphocyte epigenome undergoes DNA methylation changes during PGIA development, which is convincingly supported by the results of our animal studies (FIG. 1(A)). The genome-wide DNA methylation and gene expression studies will be extended in order to characterize RA-associated epigenome profile alterations and accompanying gene expression changes. Genomic DNA and total RNA will be isolated from B cells purified from healthy donors and RA patients. Regarding patient selection, special attention will be given to newly diagnosed patients who have had symptoms for less than 3 months. The focus will be on DMARD-naive RA patients because we have observed that various treatments could significantly alter the gene expression pattern of epigenetic modifiers. Seventy human subjects will be investigated including 50 RA patients and 20 control individuals.

Genome-Wide Histone Methylation Profiling.

Genome-wide histone methylation profiling using arthritic mouse models will be used to provide new information regarding RA pathology. Genome-wide DNA methylation analysis (i.e., capturing hypermethylated DNA fractions using the MIRA method) will be determined, NGS analysis (including library generation and amplification, sequencing data collection and normalization), and subsequent bioinformatics analyses. The NGS analyses will provide two lists: one with the genomic coordinates of the differentially methylated regions and another with the genes showing altered expression. Regions and genes that are similarly methylated and expressed in arthritic mouse and human B cells will be sought. It is expected that only a handful of common differentially expressed genes and methylated regions will be identified. The DNA methylation status and gene expression levels of these genes will be verified by individual bisulfite sequencing and qRT-PCR assays. Once we have the verified list of common targets, epigenetic data gained from the proposed drug-treatment experiments will be checked It will be determined whether drug treatments that proved to be effective on PGIA also changed the methylation status of the common regions (i.e., shared by PGIA and RA). If there is a link between the epigenetic status of the common regions with the effective drug treatments in mice, then it will be a strong indication that the given drug can be also used to reactivate those genes in RA. These proposed epigenetic studies will provide compelling evidence regarding the similarity of the PGIA and RA pathogeneses, making the consideration of introducing DNA and histone methylation blockers in RA therapy reasonable.

Data Analysis.

DNA methylation and histone modification peaks will be identified as regions with a minimum of 350 bp separated by a maximum of 250 bp with a filtered log 2 ratio greater than the 95th percentile of the log ratios on the entire array. The identified peaks will be mapped relative to known transcripts defined in the HG19 Refseq and CpG island databases. To identify targets that are specifically methylated in RA samples, a transcript must have methylation peaks in a majority of the RA samples (>75%) but not in control samples (<10%). A two-part permutation test will be applied for the marker discovery study to provide a reasonable statistical power for the analysis of microarray data since sample size is limited.

An embodiment described herein will characterize statistical and power analysis. In an aspect of the embodiment, descriptive statistics will be used to determine group means, standard deviations and standard errors of the means. Intergroup comparisons of results obtained from in vitro studies and in vivo experiments (e.g., scores and onset of arthritis, antibody responses, the results of qRT-PCR analyses, etc.) will be made using parametric or non-parametric methods, as appropriate. In vitro and in vivo results will be analyzed using Student's t-test or Mann-Whitney test to compare the means of two groups and one-way ANOVA using Fisher's least significant difference post hoc tests for multiple comparisons. All statistical analyses will be performed using SPSS (version 16.0) statistical software package (SPSS, Chicago, Ill.). Statistical power analyses will be performed using The R Foundation for Statistical Computing (http://www.r-project.org; ISBN 3-900051-07-0, 2009-04-17) R2.9.0 software package.

What is claimed:

1. A method for treating-an- rheumatoid arthritis in a patient comprising:
   administering to the patient in need thereof, a combination of a pharmaceutically effective amount of a DNA methylation inhibitor wherein the DNA methylation inhibitor is selected from the group consisting of:
   P1 4-Amino-1-(β-D-ribofuranosyl)-1,3,5-triazin-2(1H)-one (azacitidine or AzaC), 2'-Deoxy-5-azacytidine, 4-Amino-1-(2-deoxy-β-D-ribofuranosyl)-1,3,5-triazin-2(1H)-one (5-aza-2'-deoxycytidine)(dAzaC), N-[4-[(2-amino-6-methyl-4-pyrimidinyl)amino]phenyl]-4-(4-quinolinylamino)-benzamide (SGI-1027), epigallocatechin-3-gallate (EGCG), N-phthaloyl-1-tryptophan (RG108), caffeic acid, chlorogenic acid, hydralazine hydrochloride, procainamide hydrochloride, procaine hydrochloride, and 2-Amino-6-[(4-bromo-2-thienyl)methoxy]-9H-purine) (lomeguatrib); and
   a pharmaceutically effective amount of a histone methylation inhibitor wherein the histone methylation inhibitor is selected from the group consisting of:
   1-cyclopentyl-N-[(1,2-dihydro-4,6-dimethyl-2-oxo-3-pyridinyl)methyl]-6-[4-(4-morpholinylmethyl)phenyl]-1H-indazole-4-carboxamide (EPZ005687), 7-[5-Deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine (EPZ004777), N-[(1,2-dihydro-4,6-dimethyl-2-oxo-3-pyridinyl)methyl]-3-methyl-1-[(1S)-1-methylpropyl]-6-[6-(1-piperazinyl)-3-pyridinyl]-1H-indole-4-carboxamide (GSK126), N4-(1-benzylpiperidin-4-yl)-N2-(3-(dimethylamino)propyl)-6,7-dimethoxyquinazoline-2,4-diamine (E11), 2-(Hexahydro-4-methyl-1H-1,4-diazepin-1-yl)-6,7-dimethoxy-N-[1-(phenylmethyl)-4-piperidinyl]-4-quinazolinamine trihydrochloride (BIX01294), N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide (GSK343), N-[(1,2-dihydro-4,6-dimethyl-2-oxo-3-pyridinyl)methyl]-3-methyl-1-(1-methylethyl)-6-[6-(4-methyl-1-piperazinyl)-3-pyridinyl]-1H-indole-4-carboxamide (GSK503), N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide (EPZ6438), chaetocin, and
   ((R)—N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205); and
   reversing arthritis specific epigenetic changes.

2. The method according to claim 1, wherein the DNA methylation inhibitor is administered orally, nasally, topically, parenterally, systemically or peripherally.

3. The method according to claim 1, wherein the DNA methylation inhibitor is administered at a dose <70 mg/m$^2$.

4. The method according to claim 1, wherein the DNA methylation inhibitor is administered at a dose <60 mg/m$^2$.

5. The method according to claim 1, wherein the DNA methylation inhibitor is administered at a dose <50 mg/m$^2$.

6. The method according to claim 1, wherein the DNA methylation inhibitor is administered at a dose <40 mg/m$^2$.

7. The method according to claim 1, wherein the DNA methylation inhibitor is administered at a dose <30 mg/m$^2$.

8. The method according to claim 1, wherein the DNA methylation inhibitor is administered at a dose <20 mg/m$^2$.

9. The method according to claim 1, wherein the DNA methylation inhibitor is administered at a dose of 1 to 15 mg/m$^2$.

10. The method according to claim 1, wherein the arthritis specific epigenetic changes comprise downregulation of AhR gene expression, down regulation of Arnt gene expression, downregulation of Phf19 gene expression and down regulation of cytokine gene expression.

11. The method according to claim 10, wherein the cytokine genes comprise IFNy, Ifnar1, IL-10, IL-12A, IL1 R2, IL-4, IL-6, TGFβ31, TNFαa, TNFβ.

* * * * *

UNITED STATES PATENT AND TRADEMARK OFFICE
CERTIFICATE OF CORRECTION

| | |
|---|---|
| PATENT NO. | : 11,992,500 B2 |
| APPLICATION NO. | : 17/050526 |
| DATED | : May 28, 2024 |
| INVENTOR(S) | : Tibor A. Rauch et al. |

It is certified that error appears in the above-identified patent and that said Letters Patent is hereby corrected as shown below:

In the Claims

Column 39, Line 43, delete "-an-";
      Line 49, delete "P1".

Signed and Sealed this
Nineteenth Day of November, 2024

Katherine Kelly Vidal
*Director of the United States Patent and Trademark Office*